(12) United States Patent
De Peretti et al.

(10) Patent No.: US 8,148,370 B2
(45) Date of Patent: Apr. 3, 2012

(54) POLYSUBSTITUTED DERIVATIVES OF 2-ARYL-6-PHENYL-IMIDAZO[1,2-A]PYRIDINES, AND PREPARATION AND THERAPEUTIC USE THEREOF

(75) Inventors: Danielle De Peretti, Paris (FR); Yannick Evanno, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/881,805

(22) Filed: Sep. 14, 2010

(65) Prior Publication Data

US 2011/0065699 A1    Mar. 17, 2011

Related U.S. Application Data

(63) Continuation of application No. PCT/FR2009/000297, filed on Mar. 20, 2009.

(30) Foreign Application Priority Data

Mar. 21, 2008    (FR) ...................... 08 01580

(51) Int. Cl.
  *A61K 31/44*  (2006.01)
  *C07D 491/02* (2006.01)
  *C07D 498/02* (2006.01)
  *C07D 413/00* (2006.01)
(52) U.S. Cl. .................... 514/233.2; 514/300; 546/121; 544/127
(58) Field of Classification Search ................ 546/121; 514/233.2, 300; 544/127
  See application file for complete search history.

(56) References Cited

U.S. PATENT DOCUMENTS

| | | | |
|---|---|---|---|
| 7,915,284 B2 * | 3/2011 | Garcia et al. ................. | 514/300 |
| 2011/0065727 A1 * | 3/2011 | De Peretti et al. ............ | 514/256 |
| 2011/0065745 A1 * | 3/2011 | De Peretti et al. ............ | 514/300 |

FOREIGN PATENT DOCUMENTS

| | | |
|---|---|---|
| FR | 2903105 A1 | 1/2008 |
| FR | 2903107 A1 | 1/2008 |
| WO | 2008034974 * | 3/2008 |
| WO | WO2008/034974 A1 | 3/2008 |

OTHER PUBLICATIONS

International Search Report dated Sep. 24, 2009 issued in PCT/FR2009/000297.

* cited by examiner

*Primary Examiner* — Janet Andres
*Assistant Examiner* — Niloofar Rahmani
(74) *Attorney, Agent, or Firm* — Scully, Scott, Murphy & Presser, P.C.

(57) ABSTRACT

Compounds of formula (I):

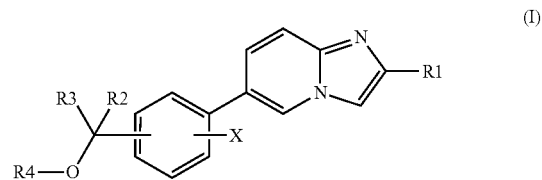

wherein $R_1$, $R_2$, $R_3$, $R_4$ and X are as defined in the disclosure, or an acid addition salt thereof, and the therapeutic use and process of synthesis thereof.

19 Claims, No Drawings

POLYSUBSTITUTED DERIVATIVES OF 2-ARYL-6-PHENYL-IMIDAZO[1,2-A]PYRIDINES, AND PREPARATION AND THERAPEUTIC USE THEREOF

This application is a continuation of International application No. PCT/FR2009/000297, filed Mar. 20, 2009, which is incorporated herein by reference in its entirety; which claims the benefit of priority of French Patent Application No. 0801580, filed Mar. 21, 2008.

The present invention relates to polysubstituted 2-aryl-6-phenylimidazo[1,2-a]pyridine derivatives, to their preparation and to their therapeutic application in the treatment or prevention of diseases involving Nurr-1 nuclear receptors, also known as NR4A2, NOT, TINUR, RNR-1 and HZF3.

A subject-matter of the present invention is the compounds of formula (I):

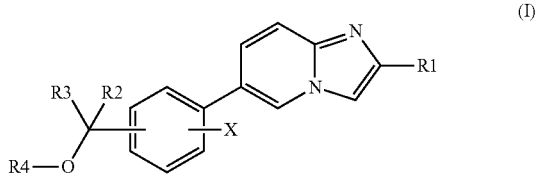

in which:

$R_1$ represents:
  a phenyl group or a naphthyl group, it being possible for these two groups optionally to be substituted by one or more atoms or groups chosen, independently of one another, from the following atoms or groups: halogen, $(C_1\text{-}C_{10})$alkyl, halo$(C_1\text{-}C_{10})$alkyl, $(C_1\text{-}C_{10})$alkoxy, halo$(C_1\text{-}C_{10})$alkoxy, $(C_1\text{-}C_{10})$thioalkyl, —S(O)$(C_1\text{-}C_{10})$alkyl, —S(O)$_2(C_1\text{-}C_{10})$alkyl, hydroxyl, cyano, nitro, hydroxy$(C_1\text{-}C_{10})$alkylene, NRaRb$(C_1\text{-}C_{10})$alkylene, $(C_1\text{-}C_{10})$alkoxy$(C_1\text{-}C_{10})$alkyleneoxy, NRaRb, CONRaRb, SO$_2$NRaRb, NRcCORd, OC(O)NRaRb, OCO$(C_1\text{-}C_{10})$alkyl, NRcC(O)ORe, NRcSO$_2$Re, aryl$(C_1\text{-}C_{10})$alkylene, monocyclic aryl or monocyclic heteroaryl, the monocyclic aryl or monocyclic heteroaryl optionally being substituted by one or more substituents chosen from a halogen or a $(C_1\text{-}C_{10})$alkyl, halo$(C_1\text{-}C_{10})$alkyl, $(C_1\text{-}C_{10})$alkoxy, halo$(C_1\text{-}C_{10})$alkoxy, NRaRb, hydroxyl, oxo, nitro, cyano or OCO$(C_1\text{-}C_{10})$alkyl group;

X represents from 1 to 4 substituents which are identical to or different from one another and which are chosen from halogen, $(C_1\text{-}C_{10})$alkyl, $(C_1\text{-}C_{10})$alkoxy, NRaRb, cyano or nitro, it being possible for the $(C_1\text{-}C_{10})$alkyl to be optionally substituted by one or more groups chosen from a halogen, $(C_1\text{-}C_{10})$alkoxy, halo$(C_1\text{-}C_{10})$alkoxy, NRaRb or hydroxyl;

$R_2$ and $R_3$ represent, independently of one another,
  a hydrogen atom,
  a $(C_1\text{-}C_{10})$alkyl group, this group being optionally substituted by an Rf group;
  an aryl group, optionally substituted by one or more substituents chosen from a halogen or a $(C_1\text{-}C_{10})$alkyl, halo$(C_1\text{-}C_{10})$alkyl, $(C_1\text{-}C_{10})$alkoxy, halo$(C_1\text{-}C_{10})$alkoxy, NRaRb, hydroxyl, nitro or cyano group;

$R_2$ and X can together form, with the carbon atoms which carry them, a carbon ring of 5 to 7 carbon atoms;

$R_4$ represents:
  a hydrogen atom,
  a $(C_1\text{-}C_{10})$alkyl group, this group being optionally substituted by an Rf group;
  an aryl group, optionally substituted by one or more substituents chosen from a halogen or a $(C_1\text{-}C_{10})$alkyl, halo$(C_1\text{-}C_{10})$alkyl, $(C_1\text{-}C_{10})$alkoxy, halo$(C_1\text{-}C_{10})$alkoxy, NRaRb, hydroxyl, nitro, cyano, $(C_1\text{-}C_{10})$alkyl(CO)—, CONRaRb, NRcCORd, OC(O)NRaRb, OCO$(C_1\text{-}C_{10})$alkyl, NRcC(O)ORe or aryl group, the aryl being optionally substituted by one or more substituents chosen from a halogen or a $(C_1\text{-}C_{10})$alkyl, halo$(C_1\text{-}C_{10})$alkyl, $(C_1\text{-}C_{10})$alkoxy, halo$(C_1\text{-}C_{10})$alkoxy, NRaRb, hydroxyl, nitro or cyano group;

Ra and Rb represent, independently of one another,
  a hydrogen atom or a $(C_1\text{-}C_{10})$alkyl, aryl$(C_1\text{-}C_{10})$alkylene or aryl group;
  or Ra and Rb together form, with the nitrogen atom which carries them, an azetidine, pyrrolidine, piperidine, azepine, morpholine, thiomorpholine, piperazine or homopiperazine group, this group being optionally substituted by a $(C_1\text{-}C_{10})$alkyl, aryl or aryl$(C_1\text{-}C_{10})$alkylene group;

Rc and Rd represent, independently of one another,
  a hydrogen atom or a $(C_1\text{-}C_{10})$alkyl, aryl$(C_1\text{-}C_{10})$alkylene or aryl group;
  or Rc and Rd together form a $(C_2\text{-}C_5)$alkylene group;

Re represents
  a $(C_1\text{-}C_{10})$alkyl, aryl$(C_1\text{-}C_{10})$alkylene or aryl group;
  or Rc and Re together form a $(C_2\text{-}C_5)$alkylene group;

Rf represents
  a halogen atom or a $(C_1\text{-}C_{10})$alkoxy, halo$(C_1\text{-}C_{10})$alkoxy, hydroxyl, cyano, NRaRb, C(O)NRaRb, NRcCORd, OC(O)NRaRb, OCO$(C_1\text{-}C_{10})$alkyl, NRcCOORe, SO$_2$NRaRb, NRcSO$_2$Re, aryl$(C_1\text{-}C_{10})$alkylene or aryl group, the aryl being optionally substituted by one or more substituents chosen from a halogen or a $(C_1\text{-}C_{10})$alkyl, halo$(C_1\text{-}C_{10})$alkyl, $(C_1\text{-}C_{10})$alkoxy, halo$(C_1\text{-}C_{10})$alkoxy, NRaRb, hydroxyl, nitro, cyano or OCO$(C_1\text{-}C_{10})$alkyl group;

in the form of the base or of an addition salt with an acid.

The compounds of formula (I) can comprise one or more asymmetric carbon atoms. They can thus exist in the form of enantiomers or diastereoisomers. These enantiomers and diastereoisomers, and their mixtures, including their racemic mixtures, come within the invention.

The compounds of formula (I) can exist in the form of bases or of addition salts with acids. Such addition salts come within the invention.

These salts can be prepared with pharmaceutically acceptable acids but the salts of other acids, for example of use in the purification or the isolation of the compounds of formula (I), also come within the invention.

The compounds of formula (I) can also exist in the form of hydrates or solvates, namely in the form of combinations or associations with one or more molecules of water or with a solvent. Such hydrates and solvates also come within the invention.

In the context of the present invention:
  a $(C_x\text{-}C_t)$ group is understood to mean a group comprising between x and t carbon atoms;
  a halogen is understood to mean a fluorine, a chlorine, a bromine or an iodine;
  an alkyl group is understood to mean a saturated, linear, branched or cyclic, aliphatic group optionally substituted by a saturated, linear, branched or cyclic, alkyl group. Mention may be made, by way of examples, of the methyl, ethyl, propyl, isopropyl, butyl, isobutyl, tert-butyl, cyclopropyl, cyclobutyl, cyclopentyl, cyclohexyl, methylcyclopropyl or cyclopropylmethyl groups, and the like;

an alkylene group is understood to mean a divalent alkyl group;

an alkoxy group is understood to mean an —O-alkyl radical where the alkyl group is as defined above;

a haloalkyl group is understood to mean an alkyl group substituted by one or more identical or different halogen atoms. Mention may be made, by way of examples, of the $CF_3$, $CH_2CF_3$, $CHF_2$ or $CCl_3$ groups.

a haloalkoxy group is understood to mean an —O-alkyl radical where the alkyl group is as defined above and is substituted by one or more identical or different halogen atoms. Mention may be made, by way of examples, of the $OCF_3$, $OCHF_2$ or $CCl_3$ groups;

a thioalkyl group is understood to mean an S-alkyl radical where the alkyl group is as defined above;

an aryl group is understood to mean a mono- or bicyclic aromatic group comprising from 6 to 10 atoms. Mention may be made, by way of examples of aryl groups, of the phenyl and naphthyl groups;

a heteroaryl group is understood to mean a mono- or bicyclic aromatic group comprising from 5 to 10 atoms, including from 1 to 4 heteroatoms chosen from N, O and S. Mention may be made, by way of examples of monocyclic heteroaryl groups, of pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine.

the sulphur and nitrogen atoms can be in the oxidized state (N-oxide, sulphoxide, sulphone).

Among the compounds of formula (I) which are subject-matters of the invention, a first group of compounds is composed of the compounds for which:

$R_1$ represents a phenyl group or a naphthyl group optionally substituted by one or more atoms or groups chosen, independently of one another, from halogen atoms or $(C_1-C_{10})$alkyl, $(C_1-C_{10})$alkoxy, nitro, —$S(O)_2(C_1-C_{10})$alkyl, halo$(C_1-C_{10})$alkyl, cyano, $(C_1-C_{10})$thioalkyl, NRaRb, NRcCORd, hydroxy$(C_1-C_{10})$alkylene, NRcSO$_2$Re, CONRaRb, NRcC(O)ORe, SO$_2$NRaRb or NRaRb$(C_1-C_{10})$alkylene groups;

Ra and Rb represent, independently of one another, a hydrogen atom or a $(C_1-C_{10})$alkyl group;

or Ra and Rb together form, with the nitrogen atom which carries them, an azetidinyl, pyrrolidinyl or morpholinyl group;

Rc and Rd represent, independently of one another, a hydrogen atom or a $(C_1-C_{10})$alkyl group;

Re represents a $(C_1-C_{10})$alkyl group;

the other substituents being as defined above.

Among the compounds of formula (I) which are subject-matters of the invention, a second group of compounds is composed of the compounds for which:

$R_1$ represents a phenyl group or a naphthyl group optionally substituted by one or more atoms or groups chosen, independently of one another, from halogen atoms, methyl, methoxy, nitro, methylsulphonyl, trifluoromethyl, cyano, methylthio, pyrrolidinyl, —NHCOCH$_3$, hydroxymethyl, —NHSO$_2$CH$_3$, —CON(CH$_3$)$_2$, —NHC(O)OCH$_3$, —C(O)NHCH$_3$, morpholinyl, —NHC(O)-isopropyl, —SO$_2$N(CH$_3$)$_2$ or pyrrolidinylethyl;

the other substituents being as defined above.

Among the compounds of formula (I) which are subject-matters of the invention, a third group of compounds is composed of the compounds for which:

$R_1$ represents a phenyl group or a naphthyl group, the phenyl group being optionally substituted in the 2, 3 or 4 position by one or more atoms or groups chosen, independently of one another, from halogen atoms, methyl, methoxy, nitro, methylsulphonyl, trifluoromethyl, cyano, methylthio, pyrrolidinyl, —NHCOCH$_3$, hydroxymethyl, —NHSO$_2$CH$_3$, —CON(CH$_3$)$_2$, —NHC(O)OCH$_3$, —C(O)NHCH$_3$, morpholinyl, —NHC(O)-isopropyl, —SO$_2$N(CH$_3$)$_2$ or pyrrolidinylethyl;

the other substituents being as defined above.

Among the compounds of formula (I) which are subject mattes of the invention, a fourth group of compounds is composed of the compounds for which:

X represents 1 or 2 substituents, identical to or different from one another, chosen from halogen, $(C_1-C_{10})$alkyl or $(C_1-C_{10})$alkoxy, it being possible for the $(C_1-C_{10})$alkyl group to be optionally substituted by a hydroxyl group;

$R_2$ and X can together form, with the carbon atoms which carry them, a carbon ring of 5 or 6 carbon atoms;

the other substituents being as defined above.

Among the compounds of formula (I) which are subject-matters of the invention, a fifth group of compounds is composed of the compounds for which:

X represents 1 or 2 substituents, identical to or different from one another, chosen from halogen atoms or the methyl, methoxy or hydroxymethyl groups;

$R_2$ and X can together form, with the carbon atoms which carry them, a carbon ring of 5 or 6 carbon;

the other substituents being as defined above.

Among the compounds of formula (I) which are subject-matters of the invention, a sixth group of compounds is composed of the compounds for which:

$R_2$ and $R_3$ represent, independently of one another, a hydrogen atom or a $(C_1-C_{10})$alkyl group;

the other substituents being as defined above.

Among the compounds of formula (I) which are subject-matters of the invention, a seventh group of compounds is composed of the compounds for which:

$R_2$ and $R_3$ represent, independently of one another, a hydrogen atom or a methyl group;

the other substituents being as defined above.

Among the compounds of formula (I) which are subject-matters of the invention, an eighth group of compounds is composed of the compounds for which:

$R_4$ represents a hydrogen atom or a $(C_1-C_{10})$alkyl group, this group being optionally substituted by an Rf group;

Rf represents a $(C_1-C_{10})$alkoxy group;

the other substituents being as defined above.

Among the compounds of formula (I) which are subject-matters of the invention, a ninth group of compounds is composed of the compounds for which:

$R_4$ represents a hydrogen atom, methyl or methoxyethyl;

the other substituents being as defined above.

Among the compounds of formula (I) which are subject-matters of the invention, a tenth group of compounds is composed of the compounds for which:

the substitution of the

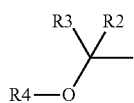

group on the phenyl ring is in the 2, 3 or 4 position; the substituents of the compounds of formula (I) being defined as above.

Among the compounds of formula (I) which are subject-matters of the invention, an eleventh group of compounds is composed of the compounds for which:

$R_1$ represents a phenyl group or a naphthyl group, optionally substituted by one or more atoms or groups chosen, independently of one another, from halogen atoms or $(C_1$-$C_{10})$alkyl, $(C_1$-$C_{10})$alkoxy, nitro, —$S(O)_2(C_1$-$C_{10})$alkyl, halo$(C_1$-$C_{10})$alkyl, cyano, $(C_1$-$C_{10})$thioalkyl, NRaRb, NRcCORd, hydroxy$(C_1$-$C_{10})$alkylene, NRcSO$_2$Re, CONRaRb, NRcC(O)ORe, SO$_2$NRaRb or NRaRb$(C_1$-$C_{10})$alkylene groups;

Ra and Rb represent, independently of one another, a hydrogen atom or a $(C_1$-$C_{10})$alkyl group;

or Ra and Rb together form, with the nitrogen atom which carries them, a pyrrolidinyl, piperidinyl or morpholinyl group;

Rc and Rd represent, independently of one another, a hydrogen atom or a $(C_1$-$C_{10})$alkyl group;

Re represents a $(C_1$-$C_{10})$alkyl group;

X represents 1 or 2 substituents, identical to or different from one another, chosen from halogen, $(C_1$-$C_{10})$alkyl, $(C_1$-$C_{10})$alkoxy, it being possible for the $(C_1$-$C_{10})$alkyl group to be optionally substituted by a hydroxyl group;

$R_2$ and X can together form, with the carbon atoms which carry them, a carbon ring of 5 or 6 carbons;

$R_2$ and $R_3$ represent, independently of one another, a hydrogen atom or a $(C_1$-$C_{10})$alkyl group;

$R_4$ represents a hydrogen atom or a $(C_1$-$C_{10})$alkyl group, this group being optionally substituted by an Rf group;

Rf represents a $(C_1$-$C_{10})$alkoxy group;

the substitution of the

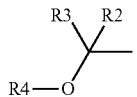

group on the phenyl ring is in the 2, 3 or 4 position;

in the form of the base or of an addition salt with an acid.

Among the compounds of formula (I) which are subject-matters of the invention, a twelfth group of compounds is composed of the compounds for which:

$R_1$ represents a phenyl group or a naphthyl group, optionally substituted by one or more atoms or groups chosen, independently of one another, from halogen atoms, methyl, methoxy, nitro, methylsulphonyl, trifluoromethyl, cyano, methylthio, pyrrolidinyl, —NHCOCH$_3$, hydroxymethyl, —NHSO$_2$CH$_3$, —CON(CH$_3$)$_2$, —NHC(O)OCH$_3$, —C(O)NHCH$_3$, morpholinyl, —NHC(O)isopropyl, —SO$_2$N(CH$_3$)$_2$ or pyrrolidinylethyl;

X represents 1 or 2 substituents, identical to or different from one another, chosen from the hydrogen or fluorine atoms or the methyl, methoxy or hydroxymethyl groups;

$R_2$ and X can together form, with the carbon atoms which carry them, a carbon ring of 5 or 6 carbons;

$R_2$ and $R_3$ represent, independently of one another, a hydrogen atom or a methyl group;

$R_4$ represents a hydrogen atom or a methyl or methoxyethyl group;

the substitution of the

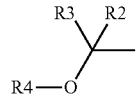

group on the phenyl ring is in the 2, 3 or 4 position;

in the form of the base or of an addition salt with an acid.

Among the compounds of formula (I) which are subject-matters of the invention, a thirteenth group of compounds is composed of the compounds for which:

$R_1$ represents a phenyl group optionally substituted by a halogen or a $(C_1$-$C_{10})$alkyl or $(C_1$-$C_{10})$alkoxy group;

X represents one or more halogen, $(C_1$-$C_{10})$alkyl, $(C_1$-$C_{10})$alkoxy or hydroxy$(C_1$-$C_{10})$alkyl;

$R_2$ and $R_3$ represent, independently of one another, a hydrogen atom or a $(C_1$-$C_{10})$alkyl group;

$R_2$ and X can together form, with the carbon atoms which carry them, a carbon ring of 6 carbon atoms;

$R_4$ represents a hydrogen atom, in the form of the base or of an addition salt with an acid.

Among the compounds of formula (I) which are subject-matters of the invention, mention may in particular be made of the following compounds:

{3-[2-(4-Chlorophenyl)imidazo[1,2-a]pyridin-6-yl]-2-fluorophenyl}methanol;

1-{3-[2-(4-Chlorophenyl)imidazo[1,2-a]pyridin-6-yl]-2-fluorophenyl}ethanol;

{3-[2-(4-Chlorophenyl)imidazo[1,2-a]pyridin-6-yl]-2,6-difluorophenyl}methanol;

1-{3-[2-(4-Chlorophenyl)imidazo[1,2-a]pyridin-6-yl]-2,6-difluorophenyl}ethanol;

1-{5-[2-(4-Chlorophenyl)imidazo[1,2-a]pyridin-6-yl]-2-fluorophenyl}ethanol;

{3-[2-(4-Chlorophenyl)imidazo[1,2-a]pyridin-6-yl]-5-methylphenyl}methanol;

{3-[2-(4-Chlorophenyl)imidazo[1,2-a]pyridin-6-yl]-5-methoxyphenyl}methanol;

7-[2-(4-Chlorophenyl)imidazo[1,2-a]pyridin-6-yl]-1,2,3,4-tetrahydronaphth-1-ol;

5-[2-(4-Chlorophenyl)imidazo[1,2-a]pyridin-6-yl]-1,2,3,4-tetrahydronaphth-1-ol;

{3-[2-(4-Chlorophenyl)imidazo[1,2-a]pyridin-6-yl]-4-methylphenyl}methanol;

{5-[2-(4-Chlorophenyl)imidazo[1,2-a]pyridin-6-yl]-2-fluorophenyl}methanol;

{5-[2-(4-Chlorophenyl)imidazo[1,2-a]pyridin-6-yl]-2-methylphenyl}methanol;

{3-[2-(4-Chlorophenyl)imidazo[1,2-a]pyridin-6-yl]-2-methylphenyl}methanol;

[2-Fluoro-4-(2-(p-tolyl)imidazo[1,2-a]pyridin-6-yl)phenyl]methanol;

[2-Fluoro-6-(2-(p-tolyl)imidazo[1,2-a]pyridin-6-yl)phenyl]methanol;

{2-Fluoro-6-[2-(3-methoxyphenyl)imidazo[1,2-a]pyridin-6-yl]phenyl}methanol;

{2-Fluoro-4-[2-(3-methoxyphenyl)imidazo[1,2-a]pyridin-6-yl]phenyl}methanol and its hydrochloride;

[2-Fluoro-4-(2-phenylimidazo[1,2-a]pyridin-6-yl)phenyl]methanol and its hydrochloride;

{2-Fluoro-3-[2-(3-methoxyphenyl)imidazo[1,2-a]pyridin-6-yl]phenyl}methanol;

[2-Fluoro-6-(2-phenylimidazo[1,2-a]pyridin-6-yl)phenyl]
methanol and its hydrochloride;
[2-Fluoro-3-(2-(p-tolyl)imidazo[1,2-a]pyridin-6-yl)phenyl]
methanol;
1-{3-[2-(4-Chlorophenyl)imidazo[1,2-a]pyridin-6-yl]-4-
fluorophenyl}ethanol;
{3-[2-(4-Chlorophenyl)imidazo[1,2-a]pyridin-6-yl]-4-
fluorophenyl}methanol;
{3-[2-(4-Chlorophenyl)imidazo[1,2-a]pyridin-6-yl]-4-
methoxyphenyl}methanol;
1-{3-[2-(4-Chlorophenyl)imidazo[1,2-a]pyridin-6-yl]-4-
methoxyphenyl}ethanol;
{3-[2-(4-Chlorophenyl)imidazo[1,2-a]pyridin-6-yl]-5-(hy-
droxymethyl)phenyl}methanol;
[2-Fluoro-3-[2-(naphth-2-yl)imidazo[1,2-a]pyridin-6-yl]
phenyl]methanol;
[2-Fluoro-3-(2-phenylimidazo[1,2-a]pyridin-6-yl)phenyl]
methanol and its hydrochloride;
(+)-1-{3-[2-(4-Chlorophenyl)imidazo[1,2-a]pyridin-6-yl]-
4-fluorophenyl}ethanol;
(−)-1-{3-[2-(4-Chlorophenyl)imidazo[1,2-a]pyridin-6-yl]-
4-fluorophenyl}ethanol;
{2-[2-(2,4-Difluorophenyl)imidazo[1,2-a]pyridin-6-yl]-6-
fluorophenyl}methanol;
{3-[2-(2,4-Difluorophenyl)imidazo[1,2-a]pyridin-6-yl]-2,6-
difluorophenyl}methanol;
2-{4-Fluoro-3-[2-(3-methoxyphenyl)imidazo[1,2-a]pyridin-
6-yl]phenyl}propan-2-ol;
1-{4-Fluoro-3-[2-(3-methoxyphenyl)imidazo[1,2-a]pyridin-
6-yl]phenyl}ethanol;
2-{3-[2-(4-Chlorophenyl)imidazo[1,2-a]pyridin-6-yl]-2,6-
difluorophenyl}propan-2-ol;
1-[4-Fluoro-2-(2-(naphth-2-yl)imidazo[1,2-a]pyridin-6-yl)
phenyl]ethanol;
6-(2,4-Difluoro-3-methoxymethylphenyl)-2-(p-tolyl)imi-
dazo[1,2-a]pyridine;
{2-Fluoro-6-[2-(4-nitrophenyl)imidazo[1,2-a]pyridin-6-yl]
phenyl}methanol;
{2,6-Difluoro-3-[2-(4-(pyrrolidin-1-yl)phenyl)imidazo[1,2-
a]pyridin-6-yl]phenyl}methanol;
{3-[2-(3,4-Difluorophenyl)imidazo[1,2-a]pyridin-6-yl]-2,6-
difluorophenyl}methanol;
{2,6-Difluoro-3-[2-(2-fluorophenyl)imidazo[1,2-a]pyridin-
6-yl]phenyl}methanol;
{3-[2-(3-Bromophenyl)imidazo[1,2-a]pyridin-6-yl]-2,6-
difluorophenyl}methanol;
{2,6-Difluoro-3-[2-(4-methylsulphonylphenyl)imidazo[1,2-
a]pyridin-6-yl]phenyl}methanol;
2-[2-Methyl-3-(2-phenylimidazo[1,2-a]pyridin-6-yl)phe-
nyl]propan-2-ol;
7-[2-(2,4-Difluorophenyl)imidazo[1,2-a]pyridin-6-yl]in-
dan-1-ol;
2-(4-Chlorophenyl)-6-[2,4-difluoro-3-[(2-methoxyethyl)
oxymethyl]phenyl]imidazo[1,2-a]pyridine;
7-[2-(2,4-Difluorophenyl)imidazo[1,2-a]pyridin-6-yl]-1-
methylindan-1-ol;
2-{3-[2-(4-Chlorophenyl)imidazo[1,2-a]pyridin-6-yl]-2-
methoxyphenyl}propan-2-ol;
1-{3-[2-(4-Chlorophenyl)imidazo[1,2-a]pyridin-6-yl]-2-
methoxyphenyl}ethanol;
{2-Fluoro-6-[2-(4-trifluoromethylphenyl)imidazo[1,2-a]py-
ridin-6-yl]phenyl}methanol;
{2-Fluoro-6-[2-(4-methoxyphenyl)imidazo[1,2-a]pyridin-6-
yl]phenyl}methanol;
{2-Fluoro-6-[2-(4-(pyrrolidin-1-yl)phenyl)imidazo[1,2-a]
pyridin-6-yl]phenyl}methanol;
{2-Fluoro-6-[2-(4-fluorophenyl)imidazo[1,2-a]pyridin-6-
yl]phenyl}methanol;
{2-[2-(3,4-Difluorophenyl)imidazo[1,2-a]pyridin-6-yl]-6-
fluorophenyl}methanol;
3-[6-(3-Fluoro-2-hydroxymethylphenyl)imidazo[1,2-a]pyri-
din-2-yl]benzonitrile;
{2-Fluoro-6-[2-(2-fluorophenyl)imidazo[1,2-a]pyridin-6-
yl]phenyl}methanol;
{2-[2-(3-Bromophenyl)imidazo[1,2-a]pyridin-6-yl]-6-
fluorophenyl}methanol;
{2-[2-(4-Chloro-3-methylphenyl)imidazo[1,2-a]pyridin-6-
yl]-6-fluorophenyl}methanol;
{2-[2-(3-Chloro-4-methylphenyl)imidazo[1,2-a]pyridin-6-
yl]-6-fluorophenyl}methanol;
{2-Fluoro-6-[2-(4-methylsulphonylphenyl)imidazo[1,2-a]
pyridin-6-yl]phenyl}methanol;
{2,6-Difluoro-3-[2-(4-methoxyphenyl)imidazo[1,2-a]pyri-
din-6-yl]phenyl}methanol;
{2,6-Difluoro-3-[2-(4-fluorophenyl)imidazo[1,2-a]pyridin-
6-yl]phenyl}methanol;
3-[6-(2,4-Difluoro-3-hydroxymethylphenyl)imidazo[1,2-a]
pyridin-2-yl]benzonitrile;
{2,6-Difluoro-3-[2-(4-chloro-3-methylphenyl)imidazo[1,2-
a]pyridin-6-yl]phenyl}methanol;
{2,6-Difluoro-3-[2-(3-chloro-4-methylphenyl)imidazo[1,2-
a]pyridin-6-yl]phenyl}methanol;
{2,6-Difluoro-3-[2-(4-methylthiophenyl)imidazo[1,2-a]py-
ridin-6-yl]phenyl}methanol;
2-[2-Chloro-3-[2-(4-chlorophenyl)imidazo[1,2-a]pyridin-6-
yl]phenyl]propan-2-ol;
1-[2-Chloro-3-[2-(4-chlorophenyl)imidazo[1,2-a]pyridin-6-
yl]phenyl]ethanol;
{2-[2-(4-Chlorophenyl)imidazo[1,2-a]pyridin-6-yl]-6-
fluorophenyl}methanol;
2-(4-Chlorophenyl)-6-[3-fluoro-2-[(2-methoxyethyl)oxym-
ethyl]phenyl]imidazo[1,2-a]pyridine;
N-{3-[6-(3-Fluoro-2-hydroxymethylphenyl)imidazo[1,2-a]
pyridin-2-yl]phenyl}acetamide;
{4-[6-(3-Fluoro-2-hydroxymethylphenyl)imidazo[1,2-a]py-
ridin-2-yl]phenyl}methanol
{3-[6-(3-Fluoro-2-hydroxymethylphenyl)imidazo[1,2-a]py-
ridin-2-yl]phenyl}methanol;
N-{4-[6-(3-Fluoro-2-hydroxymethylphenyl)imidazo[1,2-a]
pyridin-2-yl]phenyl}methanesulphonamide;
4-[6-(3-Fluoro-2-hydroxymethylphenyl)imidazo[1,2-a]pyri-
din-2-yl]-N,N-dimethylbenzamide;
Methyl {4-[6-(3-fluoro-2-hydroxymethylphenyl)imidazo[1,
2-a]pyridin-2-yl]phenyl}carbamate;
4-[6-(3-Fluoro-2-hydroxymethylphenyl)imidazo[1,2-a]pyri-
din-2-yl]-N-methylbenzamide;
N-{4-[6-(3-Fluoro-2-hydroxymethylphenyl)imidazo[1,2-a]
pyridin-2-yl]phenyl}acetamide;
{2-Fluoro-6-[2-(4-(morpholin-4-yl)phenyl)imidazo[1,2-a]
pyridin-6-yl]phenyl}methanol;
3-[6-(3-Fluoro-2-hydroxymethylphenyl)imidazo[1,2-a]pyri-
din-2-yl]-N,N-dimethylbenzenesulphonamide;
(2-Fluoro-6-{2-[4-(1-(pyrrolidin-1-yl)ethyl)phenyl]imidazo
[1,2-a]pyridin-6-yl}phenyl)methanol;
2-Fluoro-4-[6-(3-fluoro-2-hydroxymethylphenyl)imidazo
[1,2-a]pyridin-2-yl]-N,N-dimethylbenzamide;
N-{3-[6-(2,4-Difluoro-3-hydroxymethylphenyl)imidazo[1,
2-a]pyridin-2-yl]phenyl}acetamide;
{4-[6-(2,4-Difluoro-3-hydroxymethylphenyl)imidazo[1,2-
a]pyridin-2-yl]phenyl}methanol;
{3-[6-(2,4-Difluoro-3-hydroxymethylphenyl)imidazo[1,2-
a]pyridin-2-yl]phenyl}methanol;

4-[6-(2,4-Difluoro-3-hydroxymethylphenyl)imidazo[1,2-a]pyridin-2-yl]-N,N-dimethylbenzamide;
Methyl {4-[6-(2,4-difluoro-3-hydroxymethylphenyl)imidazo[1,2-a]pyridin-2-yl]phenyl}carbamate;
4-[6-(2,4-Difluoro-3-hydroxymethylphenyl)imidazo[1,2-a]pyridin-2-yl]-N-methylbenzamide;
N-{4-[6-(2,4-Difluoro-3-hydroxymethylphenyl)imidazo[1,2-a]pyridin-2-yl]phenyl}acetamide;
{2,6-Difluoro-3-[2-(4-(morpholin-4-yl)phenyl)imidazo[1,2-a]pyridin-6-yl]-phenyl}methanol;
N-{3-[6-(2,4-Difluoro-3-hydroxymethylphenyl)imidazo[1,2-a]pyridin-2-yl]phenyl}isobutyramide;
3-[6-(2,4-Difluoro-3-hydroxymethylphenyl)imidazo[1,2-a]pyridin-2-yl]-N,N-dimethylbenzenesulphonamide;
(2,6-Difluoro-3-{2-[4-(1-(pyrrolidin-1-yl)ethyl)phenyl]imidazo[1,2-a]pyridin-6-yl}phenyl)methanol;
4-[6-(2,4-Difluoro-3-hydroxymethylphenyl)imidazo[1,2-a]pyridin-2-yl]-2-fluoro-N,N-dimethylbenzamide.

In accordance with the invention, the compounds of the general formula (I) can be prepared according to the process described in Scheme 1.

group, in order to obtain the compounds of general formula (I), for example according to the method described by A. Gueiffier in *Helv. Chim. Acta,* 2001, 84, 3610-3615.

The compounds of the invention can also be prepared according to Scheme 1 by a coupling reaction, catalysed by a metal, such as palladium, between an imidazopyridine of general formula (II), in which R1 is defined as above and Y represents a halogen atom or a boron derivative, and a derivative of general formula (III') in which X is defined as above, Z represents a boron or tin derivative, if Y represents a halogen atom, or also a halogen atom, if Y represents a boron derivative, and R5' represents a carbonyl derivative $R_2CO$, in which R2 is defined as above, or else R5' represents an alkyl carboxylate, in order to obtain the compounds of general formula (IV), for example according to the method described by A. Gueiffier in *Helv. Chim. Acta,* 2001, 84, 3610-3615.

The compounds of general formula (IV) can subsequently be converted to compounds of general formula (I), for which R4 represents a hydrogen atom, by the action of an organometallic derivative, such as an organomagnesium compound, for example $R_3MgBr$, in which R3 is defined as above, or by Scheme 1

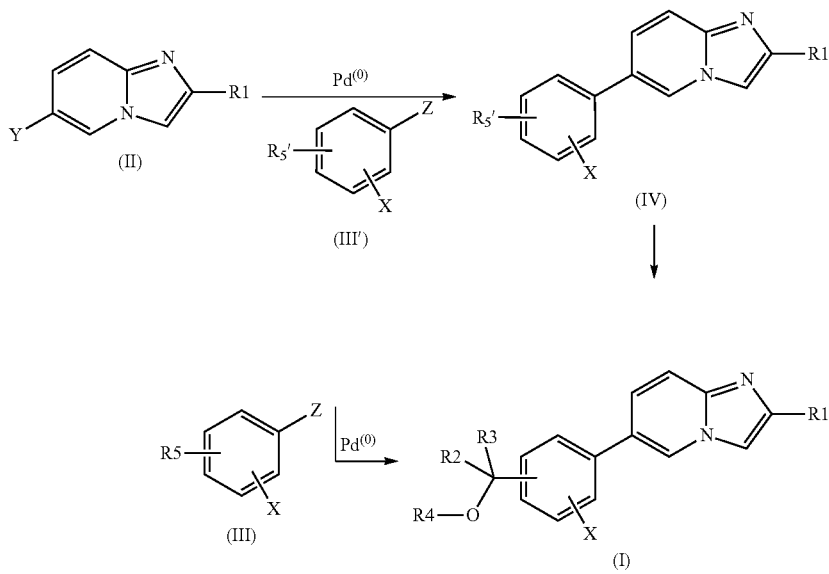

The compounds of the invention can be prepared according to Scheme 1 by a coupling reaction, catalysed by a metal, such as palladium, between an imidazopyridine of general formula (II), in which R1 is defined as above and Y represents a halogen atom or a boron derivative, and a derivative of general formula (III), in which X is defined as above, Z represents a boron or tin derivative, if Y represents a halogen atom, or else a halogen atom, if Y represents a boron derivative, and R5 represents the

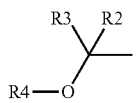

reduction of the carbonyl group using a metal hydride, for example sodium borohydride or one of its derivatives, or any other method known to a person skilled in the art.

In Scheme 1, the starting materials and the reactants, when their method of preparation is not described, are commercially available or are described in the literature or else can be prepared according to methods which are described therein or which are known to a person skilled in the art. In particular, the imidazopyridines of general formula (II) in which Y represents a boron derivative can be obtained, for example, according to the method described by E. DiMauro in *J. Org. Chem.,* 2006, 71, 3959.

In accordance with the invention, the compounds of general formula (I) can also be prepared according to the process described in Scheme 2.

Scheme 2

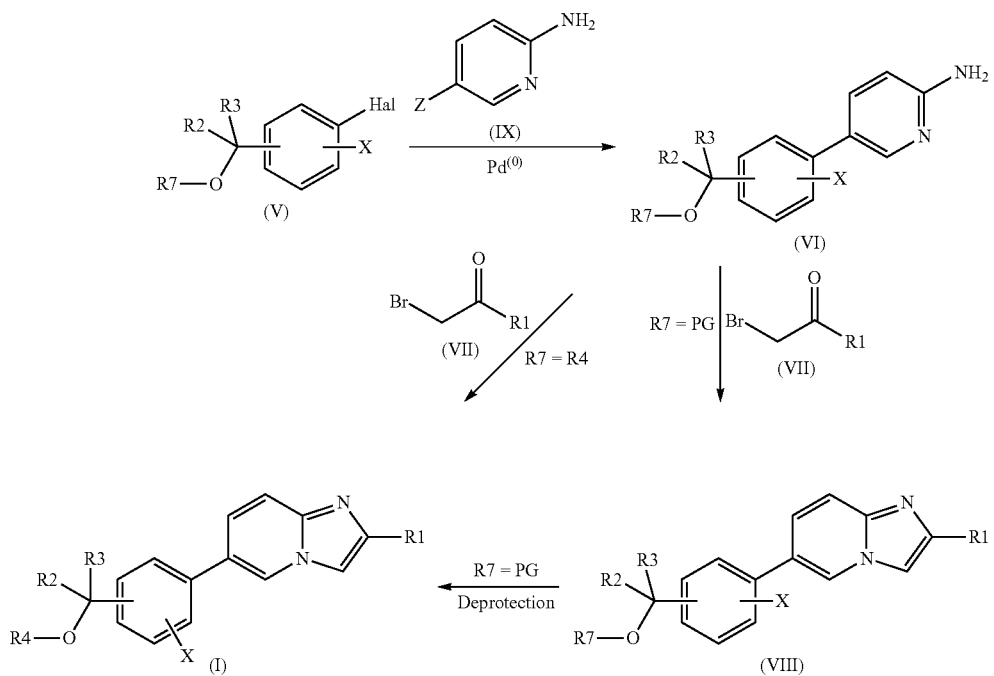

The compounds of the invention can be prepared according to Scheme 2 by a condensation reaction between an aminopyridine of general formula (VI), in which R2, R3 and X are defined as above and R7 represents R4 or a protective group (PG) for the hydroxyl functional group, and a bromoketone of general formula (VII), in which R1 is defined as above, in order to obtain an imidazopyridine of general formula (I), in which R1, R2, R3, R4 and X are defined as above, or an imidazopyridine of general formula (VIII), in which R7 represents a protective group PG, for example according to the method described by M. Fisher in *J. Med. Chem.*, 1972, 15, 982. Mention may be made, as protective group for the hydroxyl functional group, of those described, for example, by T. Greene in "*Protective Groups in Organic Synthesis*" (Wiley Interscience), for example a tert-butyldimethylsilyl group.
Finally, when R7 represents a protective group (PG) for the hydroxyl functional group, the compounds of general formula (VIII) are subjected to a deprotection reaction, as described, for example, by T. Greene in "*Protective Groups in Organic Synthesis*" (Wiley Interscience), in order to obtain the compounds of general formula (I), in which R4 represents the hydrogen atom.

The compounds of general formula (VI) can be obtained by a coupling reaction, catalysed by a metal, such as palladium, between a halogenated derivative of general formula (V), in which R2, R3, X and Hal are defined as above and R7 represents R4 or a protective group (PG) for the hydroxyl functional group, and a 2-aminopyridine (IX) substituted by a group Z which represents a boron or tin derivative, such as, for example, 5-(4,4,5,5-tetramethyl-1,3,2-dioxaborolan-2-yl) pyridin-2-ylamine.

In accordance with the invention, the compounds of general formula (I) can also be prepared according to the process described in Scheme 3.

Scheme 3

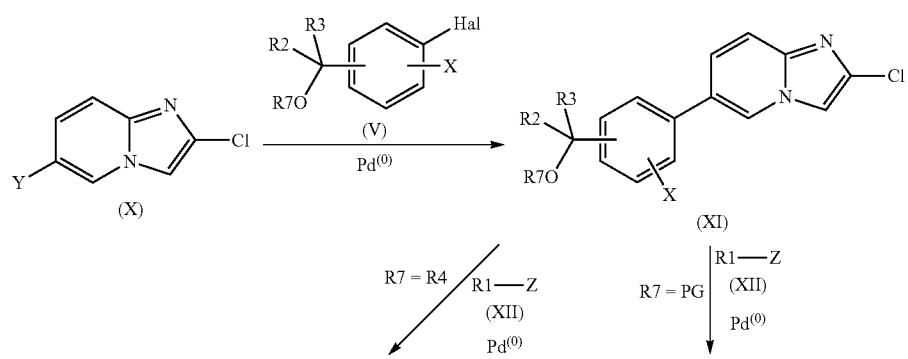

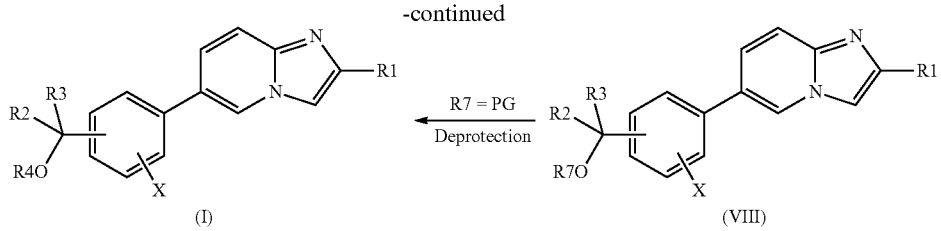

The compounds of the invention can be prepared according to Scheme 3 by a coupling reaction, catalysed by a metal, such as palladium, between an imidazopyridine of general formula (XI), in which X, R2 and R3 are defined as above and R7 represents the R4 group, and a derivative of general formula (XII), in which R1 is as defined above and Z represents a boron or tin derivative, in order to obtain the compounds of general formula (I), for example according to the method described by S. Buchwald in *J.A.C.S.*, 2005, 127, 4685.

The compounds of the invention can also be prepared according to Scheme 3 by a coupling reaction, catalysed by a metal, such as palladium, between an imidazopyridine of general formula (XI), in which X, R2 and R3 are defined as above and R7 represents a protective group (PG) for the hydroxyl functional group, such as described, for example, by T. Greene in "*Protective Groups in Organic Synthesis*" (Wiley Interscience), and a derivative of general formula (XII) in which R1 is defined as above and Z represents a boron or tin derivative, in order to obtain the compounds of general formula (VIII), for example according to the method described by S. Buchwald in *J.A.C.S.*, 2005, 127, 4685. The compounds of general formula (VIII) can subsequently be converted to compounds of general formula (I), in which R4 represents a hydrogen atom by carrying out a deprotection reaction, such as described, for example, by T. Greene in "*Protective Groups in Organic Synthesis*" (Wiley Interscience), or by any other method known to a person skilled in the art.

The imidazopyridines of general formula (XI) can be obtained by a coupling reaction, catalysed by a metal, such as palladium, between an imidazopyridine of general formula (X), in which Y represents a boron derivative, and a derivative of general formula (V), in which R2, R3 and X are defined as above, R7 represents the R4 group or a protective group (PG) for the hydroxyl functional group and Hal represents a halogen atom other than chlorine, for example according to the method described by A. Gueiffier in *Helv. Chim. Acta*, 2001, 84, 3610-3615.

In Scheme 3, the starting compounds and the reactants, when their method of preparation is not described, are commercially available or are described in the literature or else can be prepared according to methods which are described therein or which are known to a person skilled in the art. In particular, the chlorinated imidazopyridines of general formula (X) can be obtained, for example, according to the method described by C. Townsend in *Syn. Commun.*, 1997, 27, 1763-1765.

The products of formula (I) can, if desired and if necessary, be subjected to all reactions known to the person skilled in the art, in any order, in order to be converted to other products of formula (I).

Mention may be made, as examples of reactions, of: reactions for the esterification or amidation of an acid functional group, carbamoylation reactions, reactions for the hydrolysis of an ester functional group, reactions for the conversion of a hydroxyl functional group to an alkoxy functional group, coupling reactions catalysed by a transition metal, reactions for the protection of reactive functional groups, reactions for the removal of the protective groups which the protected reactive functional groups may carry, reactions for salification by an inorganic or organic acid or by a base in order to obtain the corresponding salt, or reactions for the resolution of the racemic forms to give enantiomers, the said products of formula (I) thus obtained being, if appropriate, in all the possible isomeric forms, racemic, enantiomeric and diastereoisomeric.

According to another of its aspects, another subject-matter of the invention is the compounds of formulae (IIa), (IIb), (IIc), (IId), (IIe), (IIf), (IIg), (VIa), (VIb), (Xa), (XIa) and (XIb). These compounds are of use as intermediates in the synthesis of the compounds of formula (I).

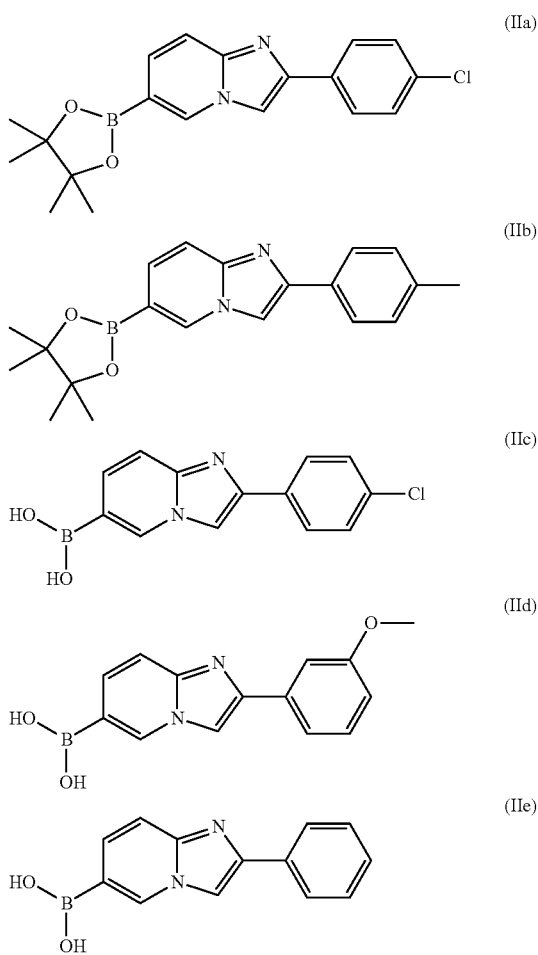

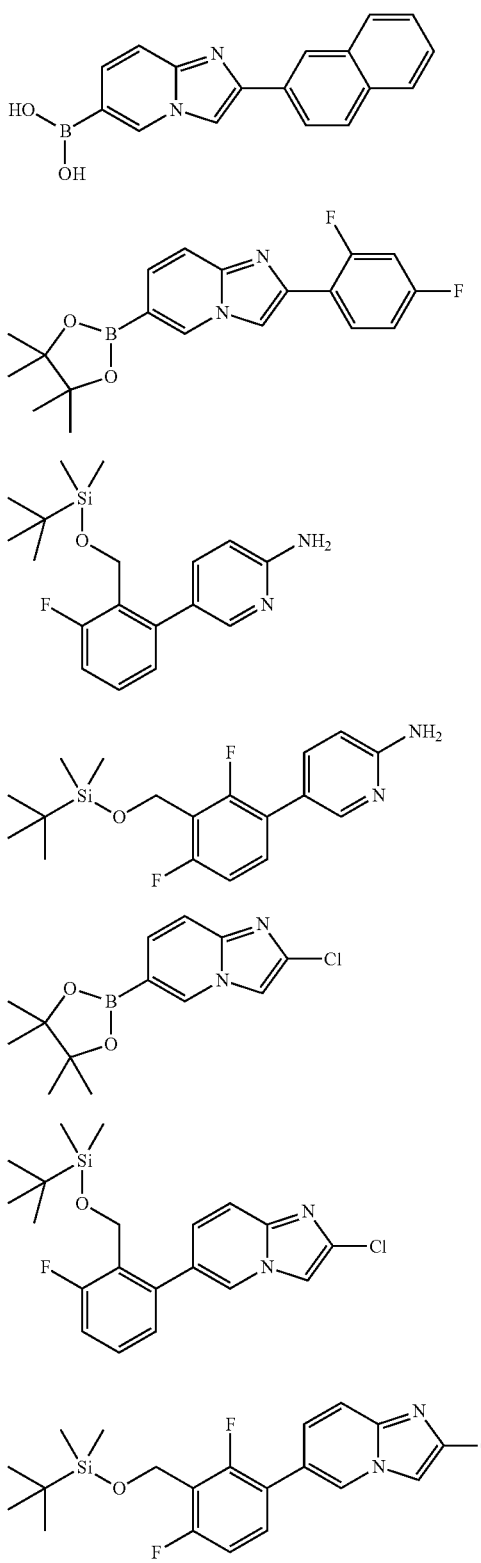

The compounds of formulae (IIa), (IIb), (IIc), (IId), (IIe), (IIf) and (IIg) can be prepared in one stage (boronic esters) or two stages (boronic acids), for example according to the process described in Examples 4 and 6. In a first stage, an aminopyridine substituted by a boron derivative, such as, for example, a 5-(4,4,5,5-tetramethyl-1,3,2-dioxaborolan-2-yl)pyridin-2-ylamine, and an α-bromoketone, such as a 2-bromo-1-(aryl)ethanone, can be condensed, for example in a solvent, such as n-propanol, in the presence of a base, such as, for example, sodium hydrogencarbonate, in order to obtain the corresponding boronic esters. Subsequently, in a second stage, the boronic esters are hydrolysed to give the corresponding boronic esters, for example in a mixture of acetone, water and hydrochloric acid.

The compounds of formulae (VIa) and (VIb) can be prepared in one stage, for example according to the process described in Examples 13 and 14. A coupling reaction catalysed by a metal, such as palladium, can be carried out between a tert-butyldimethyloxymethylbromobenzene derivative and an aminopyridine substituted by a boron derivative, such as, for example, a 5-(4,4,5,5-tetramethyl-1,3,2-dioxaborolan-2-yl)pyridin-2-ylamine.

The compound of formula (Xa) can be prepared, for example, according to the process described in Example 17. In a first stage, a condensation can be carried out between an aminopyridine substituted by a boron derivative, such as, for example, 5-(4,4,5,5-tetramethyl-1,3,2-dioxaborolan-2-yl)pyridin-2-ylamine, and ethyl 2-bromoacetate. In a second stage, the compound is subjected to a cyclization and chlorination reaction in the presence of a chlorinating agent, such as phosphorus oxychloride, which results in the compound (Xa).

The compounds of formulae (XIa) and (XIb) can be prepared by a coupling reaction, catalysed by a metal, such as palladium, between, for example, the compound (Xa) and a tert-butyldimethyloxymethylbromobenzene derivative, such as described in Examples 17 and 18.

The compounds of formulae (IIa), (IIb), (IIc), (IId), (IIe), (IIf), (IIg), (VIa), (VIb), (Xa), (XIa) and (XIb) were prepared in the powder or oil form, in the form of the base or of an addition salt with an acid. Some physicochemical data for these intermediates are collated in Table 1.

In this table, in the "Salt/base" column, "-" represents a compound in the free base form, whereas "HCl" represents a compound in the hydrochloride form and the ratio in brackets is the (base:acid) ratio.

TABLE 1

| No. | $^1$H NMR ($d_6$-DMSO, δ ppm); M + H | Salt/base |
|---|---|---|
| (IIa) | 1.35 (s, 12H); 7.35 (d, 1H); from 7.5 to 7.6 (m, 3H); 7.95 (d, 2H); 8.45 (d, 1H); 7.85 (s, 1H). M + H = 355. | — |
| (IIb) | 1.45 (s, 12H); 2.45 (s, 3H); 7.3 (d, 2H); from 7.5 to 7.7 (m, 2H); from 7.85 to 8 (m, 3H); 8.6 (s, 1H); M + H = 335 | — |
| (IIc) | From 7.6 to 7.75 (m, 2H); 7.95 (m, 1H); from 8.05 to 8.15 (m, 2H); 8.2 (m, 1H); 8.9 (s, 1H); 9.1 (s, 1H). M + H = 273. | HCl (1:1) |
| (IId) | 3.75 (s, 3H); 6.95 (d, 1H); from 7.3 to 7.65 (m, 3H); 7.8 (d, 1H); 8.05 (d, 1H); 8.75 (s, 1H); 8.9 (s, 1H). M + H = 325 | HCl (1:1) |
| (IIe) | 7.55 (m, 1H); 7.6 (m, 2H); 8.0 (m, 1H); 8.1 (m, 2H); 8.25 (d, 1H); 8.9 (s, 1H); 9.1 (s, 1H). M + H = 275 | HCl (1:1) |
| (IIf) | 7.65 (m, 2H); from 7.95 to 8.05 (m, 3H); 8.15 (m, 2H); 8.25 (d, 1H); 8.7 (s, 1H); 9.0 (s, 1H); 9.15 (m, 1H). M + H = 325. | HCl (1:1) |
| (IIg) | 1.35 (s, 12H); 7.25 (t, 1H); from 7.35 to 7.45 (m, 2H); 7.6 (d, 1H); from 8.25 to 8.35 (m, 1H); 8.45 (s, 1H); 8.9 (s, 1H). M + H = 356. | — |
| (VIa) | 0 (s, 6H); 0.85 (s, 9H); 4.5 (s, 2H); 6.05 (s, 2H); 6.45 (d, 1H); from 7.05 to 7.15 (m, 2H); from 7.3 to 7.4 (m, 1H); from 7.45 to 7.5 (m, 1H); 8.0 (d, 1H). M + H = 333 | — |

TABLE 1-continued

| No. | $^1$H NMR (d$_6$-DMSO, δ ppm); M + H | Salt/base |
|---|---|---|
| (VIb) | (CDCl$_3$): 0 (s, 6H); 0.8 (s, 9H); 4.4 (s, 2H); 6.05 (s, 2H); 6.45 (d, 1H); 7.05 (t, 1H); from 7.35 to 7.45 (m, 2H); 8.0 (s, 1H). M + H = 351 | — |
| (Xa) | 1.35 (m, 12H); 7.4 (d, 1H); 7.5 (d, 1H); 8.1 (s, 1H); 8.85 (s, 1H); M + H = 279; M.p. = 115-120° C. | — |
| (XIa) | (CDCl$_3$): 0 (s, 6H); 0.85 (s, 9H); 4.5 (s, 2H); from 7.05 to 7.1 (m, 2H); from 7.25 to 7.3 (m, 2H); 7.4 (s, 1H); 7.45 (s, 1H); 8.3 (s, 1H). M + H = 391. | — |
| (XIb) | 0.0 (s, 6H); 0.8 (s, 9H); 4.7 (s, 2H); 7.15 (t, 1H); 7.4 (d, 1H); from 7.5 to 7.6 (m, 2H); 8.0 (s, 1H); 8.65 (s, 1H). M + H = 409. | — |

The following examples describe the preparation of some compounds in accordance with the invention. These examples are not limiting and serve only to illustrate the present invention. The numbers of the compounds exemplified refer to those given in Table 2 below, in which the chemical structures of a few compounds according to the invention are illustrated.

The nomenclature employed is the nomenclature according to the IUPAC (International Union of Pure and Applied Chemistry) recommendations.

EXAMPLE 1

{3-[2-(4-Chlorophenyl)imidazo[1,2-a]pyridin-6-yl]-2-fluorophenyl}-methanol (Compound 1 of the Table)

1.1
6-Bromo-2-(4-chlorophenyl)imidazo[1,2-a]pyridine 2.33 g of 5-bromopyridin-2-ylamine and 3.14 g of 2-bromo-1-(4-chlorophenyl)-ethanone are placed in 110 ml of n-propanol in a round-bottomed flask. 1.58 g of sodium hydrogencarbonate are added. The mixture is heated at 80° C. for 16 h and allowed to cool to ambient temperature. 400 ml of water are added. The precipitate is collected by filtration, washed with water and dried in an oven under reduced pressure. 2.89 g of compound are obtained. $^1$H NMR spectrum (d$_6$-DMSO, δ in ppm): 7.4 (d, 1H); 7.5 (d, 2H); 7.6 (d, 1H); 8.0 (d, 2H); 8.4 (s, 1H); 8.9 (s, 1H). M+H=308.

1.2 3-[2-(4-Chlorophenyl)imidazo[1,2-a]pyridin-6-yl]-2-fluorobenzaldehyde 500 mg of 6-bromo-2-(4-chlorophenyl)imidazo[1,2-a]pyridine, 473 mg of 2-fluoro-3-formylbenzeneboronic acid and 93 mg of tetrakis(triphenylphosphine)palladium are placed under a stream of argon in a round-bottomed flask comprising a mixture, degassed beforehand under a stream of argon, of 5 ml of acetonitrile, 5 ml of toluene and 6 ml of a 2M sodium carbonate solution. The reaction mixture is heated at 70° C. for 21 h. After cooling, the reaction mixture is diluted with ethyl acetate and water and then the organic phase is separated, dried and evaporated under reduced pressure. The residue is purified by chromatography on silica gel, elution being carried out with a dichloromethane/ethyl acetate 98/02 mixture. 324 mg of compound are obtained.

$^1$H NMR spectrum (d$_6$-DMSO, δ in ppm): from 7.45 to 7.55 (m, 4H); 7.7 (d, 1H); 7.9 (m, 1H); from 7.95 to 8.05 (m, 3H); 8.5 (s, 1H); 8.9 (s, 1H); 10.35 (s, 1H). M+H=351.

1.3 {3-[2-(4-Chlorophenyl)imidazo[1,2-a]pyridin-6-yl]-2-fluorophenyl}methanol 162 mg of sodium borohydride are added portionwise to 150 mg of 3-[2-(4-chlorophenyl)imidazo[1,2-a]pyridin-6-yl]-2-fluorobenzaldehyde dissolved in 20 ml of methanol. The mixture is subsequently stirred at ambient temperature for 2 hours and then the solvent is evaporated under reduced pressure. The residue is taken up between water and dichloromethane and the organic phase is separated, dried over sodium sulphate and evaporated under reduced pressure. The residue is purified by chromatography on silica gel, elution being carried out with a dichloromethane/methanol 98/02 mixture. 87 mg of compound are obtained.

M.p.=200-202° C. $^1$H NMR spectrum (d$_6$-DMSO, δ in ppm): 4.65 (d, 2H); 5.35 (t, 1H); 7.35 (t, 1H); from 7.4 to 7.6 (m, 5H); 7.7 (d, 1H); 8.0 (d, 2H); 8.5 (s, 1H); 8.8 (s, 1H). M+H=353.

EXAMPLE 2

1-{3-[2-(4-Chlorophenyl)imidazo[1,2-a]pyridin-6-yl]-2-fluorophenyl}ethanol (Compound 2 of the Table)

170 mg of 3-[2-(4-chlorophenyl)imidazo[1,2-a]pyridin-6-yl]-2-fluorobenzaldehyde (compound obtained according to protocol described in Example 1.2) are placed under a stream of argon in a round-bottomed flask and dissolved in 30 ml of tetrahydrofuran. The solution is cooled to 0° C. with an ice bath and 2.60 ml of a solution, standardized beforehand at 0.56M, of methylmagnesium bromide in dibutyl ether are added dropwise. The mixture is left stirring in the ice bath for one hour and then 5 ml of a saturated aqueous ammonium chloride solution are added. The organic phase is separated and dried over sodium sulphate. The solvent is evaporated under reduced pressure. The residue is purified by chromatography on silica gel, elution being carried out with a dichloromethane/methanol mixture. 64 mg of compound are obtained. M.p.=193-195° C. $^1$H NMR spectrum (d$_6$-DMSO, δ in ppm): 1.4 (d, 3H); 5.1 (m, 1H); 5.35 (d, 1H); 7.35 (m, 1H); from 7.45 to 7.65 (m, 5H); 7.7 (d, 1H); 8.05 (d, 2H); 8.5 (s, 1H); 8.75 (s, 1H). M+H=367.

EXAMPLE 3

{3-[2-(4-Chlorophenyl)imidazo[1,2-a]pyridin-6-yl]-2,6-difluorophenyl}methanol (Compound 3 of the Table)

3.1 3-[2-(4-Chlorophenyl)imidazo[1,2-a]pyridin-6-yl]-2,6-difluorobenzaldehyde 500 mg of 6-bromo-2-(4-chlorophenyl)imidazo[1,2-a]pyridine (compound obtained according to the protocol described in Example 1.1), 364 mg of 2,4-difluoro-3-formylbenzeneboronic acid and 93 mg of tetrakis(triphenylphosphine)palladium are placed under a stream of argon in a round-bottomed flask comprising a mixture, degassed beforehand under a stream of argon, of 5 ml of acetonitrile, 5 ml of toluene and 6 ml of a 2M sodium carbonate solution. After heating at 75° C. for 24 h, 60 mg of 2,4-difluoro-3-formylbenzeneboronic acid, 18 mg of catalyst and a mixture of 2 ml of acetonitrile, 2 ml of toluene and 2 ml of a 2M sodium carbonate solution are added. Heating at 75° C. is continued for 2 hours. The reaction mixture is allowed to return to ambient temperature and is diluted with ethyl acetate and water. The organic phase is subsequently separated and dried. The solvent is concentrated under reduced pressure. The residue is purified by chromatography on silica gel, elution being carried out with a dichloromethane/ethyl acetate mixture. 340 mg of compound are obtained. $^1$H NMR spectrum (d$_6$-DMSO, δ in ppm): from 7.4 to 7.6 (m, 4H); 7.7 (d, 1H); from 8.0 to 8.1 (m, 3H); 8.5 (s, 1H); 8.85 (s, 1H); 10.35 (s, 1H). M+H=369.

3.2 {3-[2-(4-Chlorophenyl)imidazo[1,2-a]pyridin-6-yl]-2,6-difluorophenyl}-methanol 154 mg of sodium borohydride are added portionwise to 150 mg of 3-[2-(4-chlorophenyl)imidazo[1,2-a]pyridin-6-yl]-2,6-difluorobenzaldehyde dissolved in 20 ml of methanol. The mixture is subsequently stirred at ambient temperature for 3 hours and then the solvent is evaporated under reduced pressure. The residue is taken up between water and dichloromethane and then the organic phase is separated, dried over sodium sulphate and evaporated under reduced pressure. The residue is triturated from pentane, collected by filtration and then dried in an oven under reduced pressure. 67 mg of compound are obtained.

M.p.=214-216° C. $^1$H NMR spectrum (d$_6$-DMSO, δ in ppm): 4.6 (d, 2H); 5.3 (m, 1H); 7.25 (m, 1H); 7.45 (d, 1H); 7.55 (d, 2H); from 7.6 to 7.7 (m, 2H); 8.0 (d, 2H); 8.5 (s, 1H); 8.75 (s, 1H). M+H=371.

EXAMPLE 4

7-[2-(4-Chlorophenyl)imidazo[1,2-a]pyridin-6-yl]-1,2,3,4-tetrahydronaphth-1-ol (Compound 8 of the Table)

4.1 2-(4-Chlorophenyl)-6-(4,4,5,5-tetramethyl-1,3,2-dioxaborolan-2-yl)imidazo[1,2-a]pyridine 5.0 g of 5-(4,4,5,5-tetramethyl-1,3,2-dioxaborolan-2-yl)pyridin-2-ylamine and 5.30 g of 2-bromo-1-(4-chlorophenyl)ethanone are placed in 150 ml of n-propanol in a round-bottomed flask. 2.67 g of sodium hydrogencarbonate are added. The mixture is heated at 80° C. for 16 h. After cooling, the reaction mixture is concentrated under reduced pressure. 10.93 g of compound are obtained, which compound is used as is in the following stages.

$^1$H NMR spectrum (d$_6$-DMSO, δ in ppm): 1.35 (s, 12H); 7.35 (d, 1H); from 7.5 to 7.6 (m, 3H); 7.95 (d, 2H); 8.45 (d, 1H); 7.85 (s, 1H). M+H=355.

4.2 2-(4-Chlorophenyl)imidazo[1,2-a]pyridine-6-boronic acid hydro-chloride (1:1)

7.93 g of 2-(4-chlorophenyl)-6-(4,4,5,5-tetramethyl-1,3,2-dioxaborolan-2-yl)imidazo[1,2-a]pyridine are dissolved in 200 ml of acetone and 100 ml of water; 223 ml of 1N hydrochloric acid are added thereto, dropwise there with stirring, and the mixture is stirred at ambient temperature for 16 h. The reaction mixture is subsequently concentrated under reduced pressure. 4.78 g of compound are obtained, which compound is used as is in the following stages.

$^1$H NMR spectrum (d$_6$-DMSO, δ in ppm): from 7.6 to 7.75 (m, 2H); 7.95 (m, 1H); from 8.05 to 8.15 (m, 2H); 8.2 (m, 1H); 8.9 (s, 1H); 9.1 (s, 1H). M+H=273.

4.3 7-[2-(4-Chlorophenyl)imidazo[1,2-a]pyridin-6-yl]-3,4-dihydro-2H-naphth-1-one 5 ml of acetonitrile, 5 ml of toluene and 6 ml of a 2M sodium carbonate solution are introduced into a round-bottomed flask and degassed under a stream of argon. 400 mg of 2-(4-chlorophenyl)imidazo[1,2-a]pyridine-6-boronic acid, 320 mg of 7-bromo-3,4-dihydro-2H-naphth-1-one and 75 mg of tetrakis(triphenylphosphine)palladium are added. The mixture is heated at 75° C. for 16 h and then allowed to return to ambient temperature. It is taken up between ethyl acetate and water. The organic phase is separated and dried. The solvent is concentrated under reduced pressure. The residue is purified by chromatography on silica gel, elution being carried out with a dichloromethane/acetone mixture. 238 mg of compound are obtained.

$^1$H NMR spectrum (d$_6$-DMSO, δ in ppm): 2.05 (m, 2H); 2.65 (m, 2H); 3.0 (m, 2H); 7.55 (m, 3H); from 7.6 to 7.75 (m, 2H); 7.95 (m, 1H); 8.05 (d, 2H); 8.2 (s, 1H); 8.45 (s, 1H); 9.0 (s, 1H). M+H=373.

4.4 7-[2-(4-Chlorophenyl)imidazo[1,2-a]pyridin-6-yl]-1,2,3,4-tetrahydronaphth-1-ol 241 mg of sodium borohydride are added portionwise to 238 mg of 7-[2-(4-chlorophenyl)imidazo[1,2-a]pyridin-6-yl]-3,4-dihydro-2H-naphth-1-one dissolved in 25 ml of methanol. The mixture is stirred at ambient temperature for 2 hours and then the solvent is evaporated under reduced pressure. The residue is taken up between water and ethyl acetate. The organic phase is separated by settling, dried over sodium sulphate and concentrated under reduced pressure. The residue is purified by chromatography on silica gel, elution being carried out with a dichloromethane/methanol mixture. 48 mg of compound are obtained.

M.p.=232.3-233.7° C. $^1$H NMR spectrum (d$_6$-DMSO, δ in ppm): 1.75 (m, 2H); 1.95 (m, 2H); 2.75 (m, 2H); 4.65 (m, 1H); 5.2 (m, 1H); 7.2 (m, 1H); 7.5 (m, 3H); 7.6 (m, 1H); 7.7 (m, 1H); 7.75 (m, 1H); 8.05 (d, 2H); 8.45 (s, 1H); 8.85 (s, 1H). M+H=375.

EXAMPLE 5

5-[2-(4-Chlorophenyl)imidazo[1,2-a]pyridin-6-yl]-1,2,3,4-tetrahydronaphth-1-ol (Compound 9 of the Table)

5.1 5-Bromo-3,4-dihydro-2H-naphth-1-one 2.21 g of AlCl$_3$ are placed in a round-bottomed flask, to which 0.91 ml of 3,4-dihydro-2H-naphth-1-one is added over 10 min and 0.41 ml of Br$_2$ is added over 5 min, and the mixture is heated at 80° C. for 10 min. It is allowed to return to ambient temperature and a solution comprising 20 g of ice and 2.7 ml of concentrated hydrochloric acid is added thereto. The mixture is then diluted with water and diethyl ether. The organic phase is subsequently separated, dried and concentrated under reduced pressure. The residue is purified by reverse phase preparative chromatography. 172 mg of compound are obtained.

$^1$H NMR spectrum (d$_6$-DMSO, δ in ppm): 2.1 (m, 2H); 2.65 (m, 2H); 2.95 (m, 2H); 7.35 (t, 1H); 7.9 (m, 2H). M+H=226.

5.2 5-[2-(4-Chlorophenyl)imidazo[1,2-a]pyridin-6-yl]-3,4-dihydro-2H-naphth-1-one By carrying out the procedure as in Example 4.3, starting from 210 mg of 2-(4-chlorophenyl)imidazo[1,2-a]pyridine-6-boronic acid (compound obtained according to the protocol described in Example 4.2), 168 mg of 5-bromo-3,4-dihydro-2H-naphth-1-one and 39 mg of tetrakis(triphenylphosphine)palladium, 300 mg of 5-[2-(4-chlorophenyl)imidazo[1,2-a]pyridin-6-yl]-3,4-dihydro-2H-naphth-1-one are obtained.

The compound is purified by chromatography on silica gel, elution being carried out with a dichloromethane/methanol mixture. 167 mg of compound are obtained.

$^1$H NMR spectrum (d$_6$-DMSO, δ in ppm): 2.0 (m, 2H); 2.65 (m, 2H); 2.9 (m, 2H); 7.35 (d, 1H); from 7.45 to 7.55 (m, 3H); from 7.6 to 7.7 (m, 2H); from 8.0 to 8.1 (m, 3H); 8.45 (s, 1H); 8.6 (s, 1H). M+H=373.

5.3 5-[2-(4-Chlorophenyl)imidazo[1,2-a]pyridin-6-yl]-1,2,3,4-tetrahydronaphth-1-ol 169 mg of sodium borohydride are added portionwise to 167 mg of 5-[2-(4-chlorophenyl)imidazo[1,2-a]pyridin-6-yl]-3,4-dihydro-2H-naphth-1-one dissolved in 15 ml of methanol. The mixture is stirred at ambient temperature for 2 hours and then the solvent is evaporated under reduced pressure. The residue is taken up between water and ethyl acetate. The organic phase is separated by settling, dried over sodium sulphate and concentrated under reduced pressure. 106 mg of compound are obtained.

M.p.=218.1-219.6° C. $^1$H NMR spectrum (d$_6$-DMSO, δ in ppm): from 1.6 to 2.0 (m, 4H); from 2.55 to 2.7 (m, 2H); 4.65 (m, 1H); 5.2 (d, 1H); 7.2 (d, 1H); from 7.25 to 7.35 (m, 2H); 7.5 (m, 3H); 7.6 (d, 1H); 8.05 (d, 2H); 8.4 (s, 1H); 8.5 (s, 1H). M+H=375.

EXAMPLE 6

{2-Fluoro-3-[2-(3-methoxyphenyl)imidazo[1,2-a]pyridin-6-yl]phenyl}methanol (Compound 19 of the Table)

6.1 2-(3-Methoxyphenyl)-6-(4,4,5,5-tetramethyl-1,3,2-dioxaborolan-2-yl)imidazo[1,2-a]pyridine 5.00 g of 2-bromo-1-(3-methoxyphenyl)ethanone and 4.80 g of 5-(4,4,5,5-tetramethyl-1,3,2-dioxaborolan-2-yl)pyridin-2-ylamine are placed in 220 ml of n-propanol in a round-bottomed flask and 2.57 g of sodium hydrogencarbonate are added. The mixture is heated at 80° C. for 20 h and allowed to cool. The reaction mixture is concentrated under reduced pressure. The residue is taken up between water and ethyl acetate, the organic phase is separated by settling and dried over magnesium sulphate and then the solvent is concentrated. 7.47 g of compound are obtained.

$^1$H NMR spectrum (d$_6$-DMSO, δ in ppm): 1.35 (s, 12H); 3.85 (s, 3H); 6.9 (d, 1H); from 7.35 to 7.45 (m, 2H); from 7.5 to 7.6 (m, 3H); 8.45 (s, 1H); 8.8 (s, 1H). M+H=351.

6.2 2-(3-Methoxyphenyl)imidazo[1,2-a]pyridine-6-boronic acid hydro-chloride (1:1)

7.47 g of 2-(3-methoxyphenyl)-6-(4,4,5,5-tetramethyl-1,3,2-dioxaborolan-2-yl)imidazo[1,2-a]pyridine are dissolved in 236 ml of acetone and 118 ml of water; 213 ml of 1N hydrochloric acid are added thereto, dropwise and with stirring, and the mixture is stirred at ambient temperature for 24 h. The reaction mixture is subsequently concentrated under reduced pressure. The solid obtained is triturated from diethyl ether, collected by filtration and then dried in an oven under reduced pressure at 60° C. 5.80 g of compound are obtained.

$^1$H NMR spectrum (d$_6$-DMSO, δ in ppm): 3.75 (s, 3H); 6.95 (d, 1H); from 7.3 to 7.65 (m, 3H); 7.8 (d, 1H); 8.05 (d, 1H); 8.75 (s, 1H); 8.9 (s, 1H). M+H=325.

6.3 (3-Bromo-2-fluorophenyl)methanol 2.00 g of 3-bromo-2-fluorobenzaldehyde are dissolved in 98 ml of methanol; 560 mg of sodium borohydride are added portionwise thereto. The mixture is stirred at ambient temperature for 2 hours and then the solvent is evaporated under reduced pressure. The residue is taken up between water and ethyl acetate and the organic phase is separated, dried and concentrated under reduced pressure. The residue is purified by chromatography on silica gel, elution being carried out with a dichloromethane/methanol mixture. 1.56 g of compound are obtained.

$^1$H NMR spectrum (d$_6$-DMSO, δ in ppm): 4.60 (d, 2H); 5.4 (t, 1H); 7.15 (m, 1H); 7.5 (m, 1H); 7.6 (m, 1H). M+H=206.

6.4 {2-Fluoro-3-[2-(3-methoxyphenyl)imidazo[1,2-a]pyridin-6-yl]phenyl}methanol 300 mg of (3-bromo-2-fluorophenyl)methanol are dissolved in 15 ml of toluene and 5 ml of ethanol and degassed under a stream of argon for 10 min. 101 mg of tetrakis(triphenylphosphine)palladium, 580 mg of 2-(3-methoxyphenyl)imidazo[1,2-a]pyridine-6-boronic acid and 5 ml of a 2M sodium carbonate solution are subsequently added thereto. The mixture is heated at 80° C. for 16 hours and then, after cooling to ambient temperature, concentrated under reduced pressure. The residue is taken up between water and ethyl acetate and then the organic phase is separated, dried and concentrated under reduced pressure. The residue is purified by chromatography on silica gel, elution being carried out with a dichloromethane/ethyl acetate mixture. 254 mg of compound are obtained.

M.p.=143-144° C. $^1$H NMR spectrum (d$_6$-DMSO, δ in ppm): 3.85 (s, 3H); 4.65 (d, 2H); 5.35 (t, 1H); 6.95 (d, 1H); from 7.3 to 7.4 (m, 2H); 7.45 (d, 1H); from 7.5 to 7.65 (m, 4H); 7.7 (d, 1H); 8.5 (s, 1H); 8.75 (s, 1H). M+H=349.

EXAMPLE 7

1-{3-[2-(4-Chlorophenyl)imidazo[1,2-a]pyridin-6-yl]-4-fluorophenyl}ethanol (Compound 22 of the Table)

7.1 3-[2-(4-Chlorophenyl)imidazo[1,2-a]pyridin-6-yl]-4-fluorobenzaldehyde 800 mg of 6-bromo-2-(4-chlorophenyl)imidazo[1,2-a]pyridine, 437 mg of 2-fluoro-5-formylbenzeneboronic acid and 150 mg of tetrakis(triphenylphosphine)palladium are placed under a stream of argon in a round-bottomed flask comprising a mixture, degassed beforehand under a stream of argon, of 8 ml of acetonitrile, 8 ml of toluene and 10 ml of a 0.5M sodium carbonate solution. The mixture is heated at 75° C. for 5 hours and then diluted, after cooling, with a mixture of water and ethyl acetate. The organic phase is separated, dried and concentrated under reduced pressure. The residue is purified by chromatography on silica gel, elution being carried out with a dichloromethane/ethyl acetate mixture. 486 mg of compound are obtained.

$^1$H NMR spectrum (d$_6$-DMSO, δ in ppm): from 7.65 to 7.75 (m, 4H); 8.05 (d, 1H); from 8.15 to 8.25 (m, 4H); 8.35 (d, 1H); 8.7 (s, 1H). M+H=351.

7.2 1-{3-[2-(4-Chlorophenyl)imidazo[1,2-a]pyridin-6-yl]-4-fluorophenyl}ethanol 470 mg of 3-[2-(4-chlorophenyl)imidazo[1,2-a]pyridin-6-yl]-4-fluorobenzaldehyde are placed in a round-bottomed flask and dissolved in 90 ml of diethyl ether and 45 ml of tetrahydrofuran. The solution is cooled to 0° C. with an ice bath and 4 ml of a 1M solution of methylmagnesium bromide in dibutyl ether are added dropwise thereto. The mixture is stirred in the ice bath for 1 h 30 and 22 ml of a saturated aqueous ammonium chloride solution are added. The organic phase is separated, dried over magnesium sulphate and concentrated under reduced pressure. The residue obtained is purified by chromatography on silica gel, elution being carried out with a dichloromethane/methanol mixture. 401 mg of compound are obtained.

M.p.=180-182° C. $^1$H NMR (d$_6$-DMSO, δ in ppm): 1.55 (d, 3H); 5.0 (q, 1H); from 7.15 to 7.25 (m, 1H); from 7.3 to 7.6 (m, 6H); 7.75 (d, 1H); from 7.85 to 8.0 (m, 3H); 8.4 (s, 1H). M+H=367.

EXAMPLE 8

(+)-1-{3-[2-(4-Chlorophenyl)imidazo[1,2-a]pyridin-6-yl]-4-fluorophenyl}ethanol (Compound 29 of the Table)

170 mg of racemic 1-{3-[2-(4-Chlorophenyl)imidazo[1,2-a]pyridin-6-yl]-4-fluorophenyl}ethanol (compound obtained in stage 7.2) are deposited on a ChiralPAK AD LOT CFB03 20 μm 50×350 mm column. Elution is carried out with a 20/30/50 mixture of methanol, ethanol and heptane. 60 mg of the less retained compound are obtained.

[α]$_D$=+18.1 (c=0.502, methanol); +13.3 (c=0.446, DMSO).

M.p.=187-187.5° C. $^1$H NMR (d$_6$-DMSO, δ in ppm): 1.4 (s, 3H); 4.8 (m, 1H); 5.25 (s, 1H); 7.3 (t, 1H); from 7.4 to 7.55 (m, 4H); 7.6 (d, 1H); 7.7 (d, 1H); 8.0 (d, 2H); 8.5 (s, 1H); 8.8 (s, 1H).

EXAMPLE 9

(−)-1-{3-[2-(4-Chlorophenyl)imidazo[1,2-a]pyridin-6-yl]-4-fluorophenyl}ethanol (Compound 30 of the Table)

By carrying out the procedure as described in Example 8, starting from 170 mg of racemic 1-{3-[2-(4-chlorophenyl)imidazo[1,2-a]pyridin-6-yl]-4-fluorophenyl}ethanol, 62 mg of the more retained compound are obtained.

[α]$_D$=−13.2 (c=0.318, methanol); −13.5 (c=0.308, DMSO).

M.p.=184-185° C. $^1$H NMR (d$_6$-DMSO, δ in ppm): 1.4 (s, 3H); 4.8 (m, 1H); 5.25 (s, 1H); 7.3 (t, 1H); from 7.4 to 7.55 (m, 4H); 7.6 (d, 1H); 7.7 (d, 1H); 8.0 (d, 2H); 8.5 (s, 1H); 8.8 (s, 1H).

EXAMPLE 10

{2-[2-(2,4-Difluorophenyl)imidazo[1,2-a]pyridin-6-yl]-6-fluorophenyl}methanol (Compound 31 of the Table)

10.1 2-(2,4-Difluorophenyl)-6-(4,4,5,5-tetramethyl-1,3,2-dioxaborolan-2-yl)imidazo[1,2-a]pyridine By carrying out the procedure as in stage 4.1, starting from 4.76 g of 5-(4,4,5,5-tetramethyl-1,3,2-dioxaborolan-2-yl)pyridin-2-ylamine and 5.09 g of 2-bromo-1-(2,4-difluorophenyl)ethanone, 4.84 g of compound are obtained.

$^1$H NMR (d$_6$-DMSO, δ in ppm): 1.35 (s, 12H); 7.25 (t, 1H); from 7.35 to 7.45 (m, 2H); 7.6 (d, 1H); from 8.25 to 8.35 (m, 1H); 8.45 (s, 1H); 8.9 (s, 1H). M+H=356.

10.2 {2-[2-(2,4-Difluorophenyl)imidazo[1,2-a]pyridin-6-yl]-6-fluorophenyl}methanol A mixture of 9.5 ml of DME and 3.5 ml of a 2M sodium carbonate solution is degassed under argon in a pressure tube, the compound prepared in 10.1, 0.29 g of 2-bromo-6-fluorophenylmethanol and 81 mg of tetrakis(triphenylphosphine) palladium are then added, and the tube is reclosed and left stirring for 24 h in a bath thermostatically controlled at 100° C. The reaction mixture is cooled, the solvent is evaporated under reduced pressure and the residue is taken up between water and dichloromethane. The precipitate between the 2 phases is filtered off, dried and purified by chromatography on silica gel, elution being carried out with a dichloromethane/methanol mixture. 190 mg of compound are obtained and are recrystallised from a propan-2-ol/diisopropyl ether mixture. 117 mg of compound are obtained.

$^1$H NMR (d$_6$-DMSO, δ in ppm): 4.45 (d, 2H); 5.25 (t, 1H); from 7.2 to 7.35 (m, 3H); from 7.4 to 7.55 (m, 3H); 7.7 (d, 1H); 8.35 (m, 2H); 8.75 (s, 1H).

M.p.=216.5-217.5° C.

EXAMPLE 11

2-{3-[2-(4-Chlorophenyl)imidazo[1,2-a]pyridin-6-yl]-2,6-difluoro-phenyl}propan-2-ol (Compound 35 of the Table)

11.1 2-(3-Bromo-2,6-difluorophenyl)propan-2-ol 6.3 ml of a 2M solution of lithium diisopropylamide in tetrahydrofuran (standardized beforehand at 0.86M) are introduced under a stream of argon into 5 ml of tetrahydrofuran in a round-bottomed flask. The mixture is cooled to −78° C. and 0.59 ml of 1-bromo-2,4-difluorobenzene is added dropwise thereto. The mixture is stirred at −78° C. for 30 min and acetone is added via four fractions of 0.5 ml. The reaction medium is run into 20 ml of 1N hydrochloric acid after returning to ambient temperature. The organic phase, extracted with diethyl ether, is subsequently washed twice with 20 ml of water, separated, dried over magnesium sulphate and concentrated under reduced pressure. The oil obtained is purified by chromatography on silica gel, elution being carried out with a heptane/ethyl acetate mixture. 0.50 g of compound is obtained.

$^1$H NMR (d$_6$-DMSO, δ in ppm): 1.6 (m, 6H); 5.4 (s, 1H); from 6.95 to 7.15 (m, 1H); from 7.6 to 7.75 (m, 1H).

11.2 2-{3-[2-(4-Chlorophenyl)imidazo[1,2-a]pyridin-6-yl]-2,6-difluorophenyl}-propan-2-ol 500 mg of the compound obtained in stage 11.1 are dissolved in 21 ml of toluene and 7 ml of ethanol and degassed under a stream of argon for 10 min. 138 mg of tetrakis(triphenylphosphine)palladium, 799 mg of 2-(4-chlorophenyl)imidazo[1,2-a]pyridine-6-boronic acid (compound obtained according to the protocol described in Example 4.2) and 5 ml of a 2M sodium carbonate solution are subsequently added thereto. The mixture is heated at 80° C. for 1 h 30 and then, after cooling to ambient temperature, concentrated under reduced pressure. The residue is taken up between water and ethyl acetate and then the organic phase is separated, dried and concentrated under reduced pressure. The residue is purified by chromatography on silica gel, elution being carried out with a heptane/ethyl acetate mixture. The solid obtained is triturated from diisopropyl ether, collected by filtration and then dried in an oven under reduced pressure. 383 mg of compound are obtained.

M.p.=191-192° C. $^1$H NMR spectrum (d$_6$-DMSO, δ in ppm): 1.65 (s, 6H); 5.3 (s, 1H); 7.15 (m, 1H); 7.4 (m, 1H); 7.55 (m, 3H); 7.7 (m, 1H); 8.05 (d, 2H); 8.5 (s, 1H); 8.75 (s, 1H)

EXAMPLE 12

2-[2-Chloro-3-[2-(4-chlorophenyl)imidazo[1,2-a] pyridin-6-yl]phenyl]-propan-2-ol (Compound 66 of the Table)

12.1
3-Bromo-2-chloro-N-methoxy-N-methylbenzamide 500 mg of 3-bromo-2-chlorobenzoic acid are placed in 12.5 ml of tetrahydrofuran in a round-bottomed flask. The reaction mixture is cooled to 0° C. with an ice bath and then 228 mg of N,O-dimethylhydroxylamine hydrochloride, 814 mg of 1-(3-dimethylaminopropyl)-3-ethylcarbodiimide hydrochloride and 0.21 ml of pyridine are added thereto. The reaction mixture is subsequently stirred at ambient temperature for 16 h and the solvent is evaporated under reduced pressure. The residue is taken up between water and dichloromethane. The separated organic phase is subsequently washed once with a saturated ammonium chloride solution and once with a saturated sodium hydrogencarbonate solution, then dried over magnesium sulphate and concentrated under reduced pressure. 500 mg of compound are obtained.

$^1$H NMR spectrum (d$_6$-DMSO, δ in ppm): 3.3 (s, 3H); 3.45 (s, 3H); 7.35 (t, 1H); 7.5 (d, 1H); 7.85 (d, 1H).

12.2 1-(3-Bromo-2-chlorophenyl)ethanone 0.5 g of compound obtained in stage 12.1 is placed in a round-bottomed flask and dissolved in 18 ml of tetrahydrofuran. The solution is cooled to 0° C. with an ice bath and 2.7 ml of a 3M solution of methylmagnesium bromide in ethyl ether (standardized beforehand at 2M) are added dropwise thereto. The mixture is left stirring at 0° C. for 1 h and then at ambient temperature for 2 hours. The reaction mixture is subsequently hydrolysed at 0° C. with water and a saturated ammonium chloride solution and then extracted with ethyl acetate. The organic phase is separated, washed with a saturated sodium chloride solution, dried over magnesium sulphate and concentrated under reduced pressure. 0.380 g of compound is obtained.

$^1$H NMR (d$_6$-DMSO, δ in ppm): 2.6 (s, 3H); 7.4 (t, 1H); 7.65 (d, 1H); 7.95 (d, 1H).

12.3 1-[2-Chloro-3-[2-(4-chlorophenyl)imidazo[1,2-a]pyridin-6-yl]phenyl]ethanone 380 mg of compound obtained in stage 12.2 are dissolved in 16 ml of toluene and 8 ml of ethanol and degassed under a stream of argon for 10 min. 113 mg of tetrakis(triphenylphosphine)palladium, 654 mg of 2-(4-chlorophenyl)imidazo[1,2-a]pyridine-6-boronic acid (compound obtained according to the protocol described in Example 4.2) and 4.07 ml of a 2M sodium carbonate solution are subsequently added thereto. The reaction mixture is heated at 80° C. for 2 hours and then, after cooling to ambient temperature, concentrated under reduced pressure. The residue is taken up between water and ethyl acetate. The organic phase is separated by settling, washed twice with water and then twice with a saturated sodium chloride solution, dried over magnesium sulphate and concentrated under reduced pressure. The residue is purified by chromatography on silica gel, elution being carried out with a dichloromethane/ethyl acetate mixture. The solid obtained is triturated from diisopropyl ether, collected by filtration and then dried in an oven under reduced pressure. 259 mg of compound are obtained.

$^1$H NMR (d$_6$-DMSO, δ in ppm): 2.65 (s, 3H); 7.35 (d, 1H); from 7.5 to 7.65 (m, 3H); 7.7 (m, 3H); 8.05 (d, 2H); 8.5 (s, 1H); 8.7 (s, 1H).

12.4 2-[2-Chloro-3-[2-(4-chlorophenyl)imidazo[1,2-a]pyridin-6-yl]phenyl]propan-2-ol 150 mg of the compound obtained in stage 12.3 are placed under a stream of nitrogen in a round-bottomed flask and dissolved in a mixture of 26 ml of anhydrous diethyl ether and 13 ml of anhydrous tetrahydrofuran. The solution is cooled to 0° C. with an ice bath and 0.59 ml of a 3M solution of methylmagnesium bromide in ethyl ether (standardized beforehand at 2M) is added dropwise. The mixture is left stirring at 0° C. for 1 h and then at ambient temperature for 2 hours. The reaction mixture is subsequently hydrolysed at 0° C. with water and a saturated ammonium chloride solution. The organic phase is subsequently separated, dried over magnesium sulphate and concentrated under reduced pressure. The residue is purified by chromatography on silica gel, elution being carried out with a dichloromethane/ethyl acetate mixture. The solid obtained is triturated with diisopropyl ether, collected by filtration and then dried in an oven under reduced pressure. 25 mg of compound are obtained.

M.p.=230-231° C. $^1$H NMR (d$_6$-DMSO, δ in ppm): 1.65 (s, 6H); 5.35 (s, 1H); 7.3 (d, 1H); from 7.35 to 7.45 (m, 2H); 7.55 (d, 2H); 7.65 (d, 1H); 7.95 (d, 1H); 8.05 (d, 2H); 8.45 (s, 1H); 8.6 (s, 1H).

EXAMPLE 13

1-[2-Chloro-3-[2-(4-chlorophenyl)imidazo[1,2-a] pyridin-6-yl]phenyl]-ethanol (Compound 67 of the Table)

99 mg of sodium borohydride are added portionwise to 100 mg of the compound obtained in stage 12.3 dissolved in 13 ml of methanol and cooled to 0° C. The mixture is stirred at ambient temperature for 1 hour and then the solvent is evaporated under reduced pressure. The residue is taken up between water and ethyl acetate. The organic phase is separated by settling, dried over magnesium sulphate and concentrated under reduced pressure. The residue is purified by chromatography on silica gel, elution being carried out with a dichloromethane/ethyl acetate mixture. The solid obtained is triturated from diisopropyl ether, collected by filtration and then dried in an oven under reduced pressure. 73 mg of compound are obtained.

M.p.=170-172° C. $^1$H NMR (d$_6$-DMSO, δ in ppm): 1.4 (d, 3H); 5.15 (m, 1H); 5.45 (d, 1H); 7.3 (d, 1H); 7.4 (d, 1H); from 7.45 to 7.55 (m, 3H); 7.65 (d, 1H); 7.75 (d, 1H); 8.05 (d, 2H); 8.45 (s, 1H); 8.6 (s, 1H).

EXAMPLE 14

{2-Fluoro-6-[2-(4-fluorophenyl)imidazo[1,2-a]pyridin-6-yl]phenyl}-methanol (Compound 53 of the Table)

14.1 (2-Bromo-6-fluorophenyl)methanol 20.0 g (0.098 mol) of 2-bromo-6-fluorobenzaldehyde are dissolved in 500 ml of methanol and cooled in an ice bath;

3.72 g (0.098 mol) of sodium borohydride are then added portionwise thereto. The mixture is stirred under cold conditions for 1 hour and then the solid is evaporated under reduced pressure. The residue is taken up between water and dichloromethane and the organic phase is separated, dried and concentrated under reduced pressure. The residue is crystallised from pentane. 18.1 g of compound are obtained.

$^1$H NMR (CDCl$_3$, δ in ppm): 2.15 (t, 1H); 4.95 (d, 2H); from 7.05 to 7.3 (m, 2H); 7.45 (d, 1H).

14.2 (2-Bromo-6-fluorobenzyloxy(tert-butyl)dimethylsilane 15.7 g (0.076 mol) of the compound obtained above are dissolved in 230 ml of THF in a 500 ml round-bottomed flask, 7.8 g (0.115 mol) of imidazole and then 13.8 g (0.092 mol) of tert-butyldimethylchlorosilane are added and the reaction mixture is stirred for 16 hours. The solvent is then evaporated under reduced pressure, the residue is taken up between water and diethyl ether, separation by settling is carried out and the organic phase is washed with water and dried over sodium sulphate. After evaporating the solvent, 25 g of oil are collected.

$^1$H NMR (CDCl$_3$, δ in ppm): 0.0 (s, 6H); 0.8 (s, 9H); 4.7 (s, 2H); from 6.8 to 7.05 (m, 2H); 7.25 (d, 1H).

14.3 5-[2-(tert-Butyldimethylsilanyloxymethyl)-3-fluorophenyl]pyridin-2-ylamine 6.4 g of the compound obtained in 14.2, 4.40 g of 5-(4,4,5,5-tetramethyl-1,3,2-dioxaborolan-2-yl)pyridin-2-ylamine, 30 ml of a 2M sodium carbonate solution and 816 mg of [1,1'-bis(diphenylphosphino)ferrocene]dichloropalladium are dissolved in 80 ml of N,N-dimethylformamide and placed in a round-bottomed flask under a stream of argon. The mixture is heated at 80° C. for 2 h. After cooling to ambient temperature, the solvents are evaporated under reduced pressure and the residue is taken up between water and ethyl acetate. An insoluble material is removed by filtration through celite. The organic phase is separated by settling, washed with a saturated aqueous sodium chloride solution and dried over sodium sulphate. The compound is purified by chromatography, elution being carried out with a mixture of dichloromethane and methanol. 4.58 g of oil are obtained.

$^1$H NMR (CDCl$_3$, δ in ppm): 0 (s, 6H); 0.8 (s, 9H); 4.4 (s, 2H); 6.05 (s, 2H); 6.45 (d, 1H); 7.05 (t, 1H); from 7.35 to 7.45 (m, 2H); 8.0 (s, 1H). M+H=351 lacking 1H

14.4 6-[2-(tert-Butyldimethylsilanyloxymethyl)-3-fluorophenyl]-2-(4-fluorophenyl)imidazo[1,2-a]pyridine 58 mg (0.7 mmol) of sodium bicarbonate are weighed into a microwave tube. 83 mg (0.25 mmol) of the compound obtained in 14.3, in solution in 2 ml of propan-1-ol, are added thereto, followed by 0.375 mmol of 1-(4-fluorophenyl)-2-bromoethanone in solution in 1 ml of propan-1-ol. The tube is sealed and then stirred at 80° C. for 16 hours. The reaction mixture is cooled to ambient temperature, 200 mg of propanethiol on silica (Biotage Si-Thiol) are added thereto and the mixture is stirred at ambient temperature for 6 h. It is then filtered and the filtrate is evaporated under reduced pressure. The compound is used as is in the following stage.

14.5 {2-Fluoro-6-[2-(4-fluorophenyl)imidazo[1,2-a]pyridin-6-yl]phenyl}methanol The crude compound obtained in 14.4 is dissolved in 5 ml of THF comprising 0.5 mmol of tetrabutylammonium fluoride hydrate. The mixture is stirred at ambient temperature for 16 h and then the solvent is evaporated under reduced pressure. The compound is purified by chromatography. 24.9 mg of compound are obtained.

$^1$H NMR (d$_6$-DMSO, δ in ppm): 4.45 (d, 2H); 5.3 (t, 1H); 7.3 (m, 4H); from 7.4 to 7.5 (m, 2H); 7.65 (d, 1H); 8.05 (m, 2H); 8.45 (s, 1H); 8.65 (s, 1H).

EXAMPLE 15

{3-[2-(3,4-Difluorophenyl)imidazo[1,2-a]pyridin-6-yl]-2,6-difluoro-phenyl}methanol (Compound 40 of the Table)

15.1 (3-Bromo-2,6-difluorophenyl)methanol 20 g of 3-bromo-2,6-difluorobenzaldehyde are dissolved in 450 ml of methanol and cooled in an ice bath; 3.42 g of sodium borohydride are then added portionwise thereto. The mixture is stirred at ambient temperature for 1 hour and then the solvent is evaporated under reduced pressure. The residue is taken up between water and dichloromethane and the organic phase is separated, dried and concentrated under reduced pressure. The residue is crystallised from n-pentane. 14.6 g of compound are obtained.

$^1$H NMR spectrum (CDCl$_3$, δ in ppm): 2.0 (s, 1H); 4.9 (s, 2H); from 6.85 to 7.0 (m, 1H); from 7.5 to 7.65 (m, 1H).

15.2 (3-Bromo-2,6-difluorobenzyloxy)(tert-butyl) dimethylsilane 11.15 g of the compound obtained in 15.1 are dissolved in 150 ml of THF, 5.1 g of imidazole and then 9.04 g of chloro (tert-butyl)dimethylsilane are added and the mixture is stirred at ambient temperature for 24 hours. The solvent is then evaporated, the residue is taken up between water and diethyl ether, separation by settling is carried out and the organic phase is washed with water and dried over sodium sulphate. The solvent is evaporated under reduced pressure. 17.5 g of oil are obtained.

$^1$H NMR spectrum (CDCl$_3$, δ in ppm): 0.0 (s, 6H); 0.8 (s, 9H); 4.65 (s, 2H); from 6.65 to 6.7 (m, 1H); from 7.3 to 7.4 (m, 1H).

15.3 5-[3-(tert-Butyldimethylsilanyloxymethyl)-2,4-difluorophenyl]pyridin-2-ylamine 6.7 g of the compound obtained in 15.2, 4.40 g of 5-(4,4,5,5-tetramethyl-1,3,2-dioxaborolan-2-yl)pyridin-2-ylamine, 30 ml of a 2M sodium carbonate solution and 816 mg of [1,1'-bis(diphenylphosphino)ferrocene]dichloropalladium are dissolved in 80 ml of N,N-dimethylformamide and placed in a round-bottomed flask under a stream of argon. The mixture is heated at 80° C. for 2 h. After cooling to ambient temperature, the solvents are evaporated under reduced pressure, the residue is taken up between water and ethyl acetate and an insoluble material is removed by filtration through celite. The organic phase is separated by settling, washed with a saturated aqueous sodium chloride solution and dried over sodium sulphate. The compound is purified by chromatography, elution being carried out with a mixture of dichloromethane and methanol. 4.25 g of white solid are obtained.

$^1$H NMR (d$_6$-DMSO, δ in ppm): 0 (s, 6H); 0.8 (s, 9H); 4.4 (s, 2H); 6.05 (s, 2H); 6.45 (d, 1H); 7.05 (t, 1H); from 7.35 to 7.45 (m, 2H); 8.0 (s, 1H). M+H=351.

15.4 6-[3-(tert-Butyldimethylsilanyloxymethyl)-2,4-difluorophenyl]-2-(3,4-difluorophenyl)imidazo[1,2-a]pyridine 58.8 mg (0.7 mmol) of sodium bicarbonate are weighed into a microwave tube. 87.5 mg (0.25 mmol) of the compound obtained in 15.3, in solution in 2 ml of propan-1-ol, are added thereto, followed by 0.375 mmol of 2-bromo-1-(3,4-difluorophenyl)ethanone, in solution in 1 ml of propan-1-ol. The tube is sealed and then stirred at 80° C. for 16 hours. The reaction mixture is cooled to ambient temperature, 200 mg of propanethiol on silica (Biotage Si-Thiol) are added thereto and the mixture is stirred at ambient temperature for 6 h and then filtered. The residue is washed with 2 times 2 ml of propan-1-ol and the filtrate is evaporated. The compound is used as is in the following stage.

15.5 {3-[2-(3,4-Difluorophenyl)imidazo[1,2-a]pyridin-6-yl]-2,6-difluorophenyl}-methanol The crude compound obtained in 15.4 is dissolved in 5 ml of THF comprising 0.5 mmol of tetrabutylammonium fluoride hydrate. The mixture is stirred at ambient temperature for 16 h and then the solvent is evaporated under reduced pressure. The compound is purified by chromatography. 49.6 mg of compound are obtained.

$^1$H NMR ($d_6$-DMSO, δ in ppm): 4.6 (d, 2H); 5.35 (t, 1H); 7.25 (t, 1H); 7.45 (d, 1H); from 7.5 to 7.6 (m, 1H); from 7.6 to 7.7 (m, 2H); from 7.8 to 7.85 (m, 1H); from 7.95 to 8.05 (m, 1H); 8.5 (s, 1H); 8.75 (s, 1H).

EXAMPLE 16

{2-[2-(4-Chlorophenyl)imidazo[1,2-a]pyridin-6-yl]-6-fluorophenyl}-methanol (Compound 68 of the Table)

16.1 6-[2-(tert-Butyldimethylsilanyloxymethyl)-3-fluorophenyl]-2-(4-chlorophenyl)imidazo[1,2-a]pyridine 1.2 g (3.61 mmol) of the compound obtained in 14.3, 0.94 g (3.97 mmol) of 2-bromo-(4-chlorophenyl)ethanone, 0.42 g (5.05 mmol) of sodium hydrogencarbonate and 35 ml of absolute ethanol are introduced into a 100 ml three-necked flask equipped with a magnetic stirrer and maintained under a nitrogen atmosphere. After stirring at 80° C. for 18 hours, the reaction mixture is brought back to ambient temperature and concentrated under reduced pressure. The residue is then diluted with 50 ml of water and 100 ml of $CH_2Cl_2$. Separation by settling is carried out and the organic phase is dried with sodium sulphate. The solid obtained after evaporation of the solvent is purified by chromatography on a column of silica gel, elution being carried out with a mixture of dichloromethane and acetone. 1.47 g of the expected product are thus obtained.

$^1$H NMR ($d_6$-DMSO), δ (ppm): 0.0 (s, 6H); 0.8 (s, 9H); 4.5 (d, 2H); 7.05 (m, 2H); 7.3 (m, 5H); 7.55 (d, 1H); 7.75 (s, 1H); 7.85 (d, 1H); 8.35 (s, 1H).

16.2 {2-[2-(4-Chlorophenyl)imidazo[1,2-a]pyridin-6-yl]-6-fluorophenyl}methanol 1.57 g (5.99 mmol) of tetrabutylammonium fluoride are added to a solution, maintained under an inert atmosphere and stirred at ambient temperature, of 1.4 g (3 mmol) of the compound obtained in 16.1 in 50 ml of THF. After reacting at ambient temperature for 1 hour, the solvent is evaporated under reduced pressure. The residue is diluted with 20 ml of water and 50 ml of dichloromethane. Separation by settling is carried out and the aqueous phase is extracted with 2×20 ml of dichloromethane. The combined organic phases are washed three times with 20 ml of water, dried over sodium sulphate and then concentrated under reduced pressure. The resulting solid is purified by chromatography on a column of silica gel, elution being carried out with a mixture of dichloromethane and methanol. The solid obtained is recrystallized from absolute ethyl alcohol. The crystals formed are filtered off and then dried at 100° C. under reduced pressure. 0.60 g of the expected product is obtained.

$^1$H NMR ($d_6$-DMSO), δ (ppm): 4.45 (d, 2H); 5.3 (t, 1H); 7.3 (m, 2H); 7.55-7.4 (m, 4H); 7.7 (d, 1H); 8.05 (d, 2H); 8.5 (s, 1H); 8.7 (s, 1H). M.p.: 229-230° C.

EXAMPLE 17

2-(4-Chlorophenyl)-6-[3-fluoro-2-[(2-methoxyethyl)oxymethyl]phenyl]imidazo[1,2-a]pyridine (Compound 69 of the Table)

0.4 g (1.13 mmol) of the compound prepared in stage 16.2, 0.47 g (3.39 mmol) of 1-bromo-2-methoxyethane and 3.28 g (22.6 mmol) of 40% potassium fluoride on alumina are introduced into a 50 ml round-bottomed flask. The mixture is diluted with 10 ml of acetonitrile and 10 ml of N,N-dimethylformamide and then stirred at 80° C. for 4 hours. After this time, the cooled mixture is filtered. The solvent is evaporated under reduced pressure and the residue obtained is purified by chromatography on a column of silica gel, elution being carried out with a mixture of acetone and dichloromethane. The solid obtained after evaporation of the solvent under reduced pressure is washed with isopropyl ether at reflux, filtered off under cold conditions and then dried at 100° C. under reduced pressure. 120 mg of the expected product are thus obtained.

$^1$H NMR ($d_6$-DMSO), δ (ppm): 3.45 (s, 3H); 3.65 (t, 2H); 3.75 (t, 2H); 4.5 (s, 2H); 7.15 (m, 1H); 7.25 (d, 1H); 7.35 (d, 1H); 7.45 (m, 3H); 7.7 (d, 1H); 7.95 (m, 3H); 8.65 (s, 1H). M.p.=104-105° C.

EXAMPLE 18

Preparation of Compounds 70 to 81

18.1 Ethyl [2-imino-5-(4,4,5,5-tetramethyl-1,3,2-dioxaborolan-2-yl)-2H-pyridin-1-yl]acetate hydrobromide 5.0 g of 5-(4,4,5,5-Tetramethyl-1,3,2-dioxaborolan-2-yl)pyridin-2-ylamine in 7.6 ml of ethyl 2-bromoacetate are placed in a round-bottomed flask and the mixture is stirred at ambient temperature for 20 h. A precipitate is formed and is collected by filtration, washed with diethyl ether and then with ethanol and dried in an oven under reduced pressure. 8.78 g of compound are obtained.

$^1$H NMR spectrum ($d_6$-DMSO, δ in ppm): 1.3 (m, 15H to be confirmed); from 4.1 to 4.25 (m, 2H); 5.2 (s, 2H); 7.1 (d, 1H); 8.0 (d, 1H); 8.3 (s, 1H); 9.0 (s, 1H). M+H=388.

18.2 2-Chloro-6-(4,4,5,5-tetramethyl-1,3,2-dioxaborolan-2-yl)imidazo[1,2-a]pyridine (Intermediate Compound (Xa))

8.78 g of the compound obtained according to the protocol described in 18.1 are placed in 20 ml of $POCl_3$ in a round-bottomed flask. The reaction mixture is heated at 105° C. for 16 h, cooled to ambient temperature and concentrated under reduced pressure. The residue is taken up between dichloromethane and water at 0° C. and a 30% aqueous NH$_4$OH solution is added until the pH is basic. The organic phase is separated, dried over magnesium sulphate and concentrated under reduced pressure. 4.3 g of compound are obtained.

M.p.=115-120° C. $^1$H NMR spectrum (d$_6$-DMSO, δ in ppm): 1.35 (m, 12H); 7.4 (d, 1H); 7.5 (d, 1H); 8.1 (s, 1H); 8.85 (s, 1H). M+H=279.

18.3 6-[2-(tert-Butyldimethylsilanyloxymethyl)-3-fluorophenyl]-2-chloroimidazo[1,2-a]pyridine 100 ml of an 85/15 mixture of THF and water are degassed under a stream of argon and then 5.3 g of the compound prepared in 9.2, 6.07 g of 2-chloro-6-(4,4,5,5,-tetramethyl-1,2,3-dioxaborolan-2-yl)imidazo[1,2-a]pyridine, obtained as is in 18.2, 18.6 g of caesium carbonate and 466 mg of [1,1'-bis(diphenylphosphino)ferrocene]dichloropalladium are added. The mixture is stirred for 2 hours in a bath thermostatically controlled at 80° C. After cooling to ambient temperature, the solvents are evaporated under reduced pressure. The residue is taken up between water and diethyl ether. A solid is removed by filtration. The organic phase, washed twice with a saturated sodium chloride solution, is subsequently dried over sodium sulphate and concentrated under reduced pressure. The residue obtained is purified by chromatography on silica gel, elution being carried out with a dichloromethane/methanol mixture. The solid obtained is triturated from pentane, collected by filtration and then dried in an oven under reduced pressure. 4.74 g of compound are obtained.

$^1$H NMR (CDCl$_3$, δ in ppm): 0 (s, 6H); 0.85 (s, 9H); 4.5 (s, 2H); from 7.05 to 7.1 (m, 2H); from 7.25 to 7.3 (m, 2H); 7.4 (s, 1H); 7.45 (s, 1H); 8.3 (s, 1H). M+H=391.

18.4 Process for the Preparation of Compounds 70 to 81

18.4.1 0.495 mmol of palladium acetate and 0.99 mmol of S-Phos are weighed into a 100 ml round-bottomed flask purged with argon. 55 ml of degassed toluene are added thereto and the mixture is stirred in an ultrasonic bath until completely dissolved.

18.4.2 0.3 mmol of arylboronic acid is weighed into a reaction tube, 0.36 mmol of finely powdered and dried potassium phosphate, 0.5 ml of degassed anhydrous ethanol and 0.18 mmol of the compound obtained in 18.3, in solution in 2 ml of toluene, are successively added thereto and then the tube is purged with argon. 1 ml of the solution prepared in 18.4.1 is subsequently added. The tube is closed and stirred at 75° C. for 16 h. A further 0.5 ml of the solution prepared in 18.4.1 is added and the heating is extended for 10 h. The cooled solution is diluted with 5 ml of ethyl acetate, 100 mg of silica-propanethiol (Biotage Si-Thiol) are added thereto and the mixture is stirred at ambient temperature for 4 h. The solid is separated by filtration and washed with 2×2 ml of THF. The filtrate is evaporated to dryness and the residue is used as is in the following stage.

18.4.3 The compound obtained in 18.4.2, 0.36 mmol of caesium fluoride in solution of 3 ml of methanol and 21 µl of acetic acid are mixed in a reaction tube. The solution is stirred at ambient temperature for 16 hours and the solvents are subsequently evaporated. The residue is purified by HPLC, elution being carried out with an acetonitrile/water mixture.

EXAMPLE 19

Preparation of Compounds 82 to 93

19.1 6-[3-(tert-Butyldimethylsilanyloxymethyl)-2,4-difluorophenyl]-2-chloro-imidazo[1,2-a]pyridine 100 ml of an 85/15 mixture of THF and water are degassed under a stream of argon and then 5.3 g of the compound prepared in 15.2, 6.07 g of 2-chloro-6-(4,4,5,5-tetramethyl-1,2,3-dioxaborolan-2-yl)imidazo[1,2-a]pyridine, obtained as in 18.2, 18.6 g of caesium carbonate and 466 mg of [1,1'-bis(diphenylphosphino)ferrocene]dichloropalladium are added. The mixture is stirred for 2 hours in a bath thermostatically controlled at 80° C. After cooling to ambient temperature, the solvents are evaporated under reduced pressure. The residue is taken up between water and diethyl ether. A solid is removed by filtration. The organic phase, washed twice with a saturated sodium chloride solution, is subsequently dried over sodium sulphate and concentrated under reduced pressure. The residue obtained is purified by chromatography on silica gel, elution being carried out with a dichloromethane/methanol mixture. The solid obtained is triturated from pentane, collected by filtration and then dried in an oven under reduced pressure. 4.74 g of compound are obtained.

$^1$H NMR (d$_6$-DMSO, δ in ppm): 0.0 (s, 6H); 0.8 (s, 9H); 4.7 (s, 2H); 7.15 (t, 1H); 7.4 (d, 1H); from 7.5 to 7.6 (m, 2H); 8.0 (s, 1H); 8.65 (s, 1H). M+H=409.

19.2 Process for the Preparation of Compounds 82 to 93

19.2.1 0.3 mmol of arylboronic acid is weighed into a reaction tube, 0.36 mmol of finely powdered and dried potassium phosphate, 0.5 ml of degassed anhydrous ethanol and 0.18 mmol of the compound obtained in 19.1, in solution in 2 ml of toluene, are successively added thereto and then the tube is purged with argon. 1 ml of the solution prepared in 18.4.1 is subsequently added. The tube is closed and stirred at 75° C. for 16 h. A further 0.5 ml of the solution prepared in 18.4.1 is added and the heating is extended for 10 h. The cooled solution is diluted with 5 ml of ethyl acetate, 100 mg of silica-propanethiol (Biotage Si-Thiol) are added thereto and the mixture is stirred at ambient temperature for 4 h. The solid is separated by filtration and washed with 2×2 ml of THF. The filtrate is evaporated to dryness and the residue is used as is in the following stage.

19.2.2 The compound obtained in 19.2.1, 0.36 mmol of caesium fluoride in solution in 3 ml of methanol and 21 µl of acetic acid are mixed in a reaction tube. The solution is stirred at ambient temperature for 16 hours and the solvents are subsequently evaporated. The residue is purified by HPLC, elution being carried out with an acetonitrile/water mixture.

The chemical structures of the compounds of general formula (I) which are subject-matters of the invention are illustrated in Table 2.

The physicochemical characteristics of a few examples of compounds according to the invention are illustrated in Table 3 and Table 4.

In these tables:

the "R" column gives the position of substitution of the

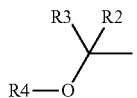

group on the phenyl ring (2, 3 or 4);

the "M.p." column gives the melting points of the products in degrees Celsius (° C.) or, when the products were isolated in the form of an amorphous solid or oil, they are characterized by their mass [M+H];

in the "Salt/base" column, "-" represents a compound in the free base form, whereas "HCl" represents a compound in the hydrochloride form and the ratio in brackets is the (base:acid) ratio;

for compounds 29 and 30, the boxes of the "Salt/base" column give the analytical result for the optical rotation of these compounds at the wavelength of 589 nm; the solvent shown in brackets corresponds to the solvent employed to carry out the measurement of the optical rotation in degrees and the letter "c" shows the concentration of the solvent in g/100 ml; DMSO means dimethyl sulphoxide;

"Ph" means phenyl; "Cl" means chlorine; "F" means fluorine; "Me" means methyl; "MeO" means methoxy; "$(F_2CH)O$" means difluoromethoxy; IsPr means isopropyl;

in the "R" column, the figure in front of the substituent gives the position of substitution of the R group on the phenyl ring;

"ND" means not determined.

TABLE 2

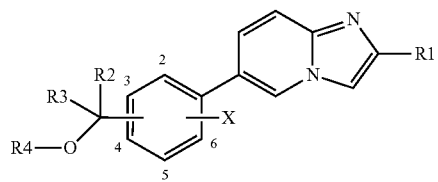

| Ex. | $R_1$ | R | $R_4$ | $R_3$ | $R_2$ | X | Salt/base |
|---|---|---|---|---|---|---|---|
| 1 | 4-Cl—Ph | 3 | H | H | — | 2-F | — |
| 2 | 4-Cl—Ph | 3 | H | Me | H | 2-F | — |
| 3 | 4-Cl—Ph | 3 | H | H | H | 2,4-$(F)_2$ | — |
| 4 | 4-Cl—Ph | 3 | H | Me | H | 2,4-$(F)_2$ | — |
| 5 | 4-Cl—Ph | 3 | H | Me | H | 4-F | — |
| 6 | 4-Cl—Ph | 3 | H | H | H | 5-Me | — |
| 7 | 4-Cl—Ph | 3 | H | H | H | 5-MeO | — |
| 8 | 4-Cl—Ph | 3 | H | H | —$(CH_2)_3$—* | | — |
| 9 | 4-Cl—Ph | 3 | H | H | —$(CH_2)_3$—* | | — |
| 10 | 4-Cl—Ph | 3 | H | H | H | 6-Me | — |
| 11 | 4-Cl—Ph | 3 | H | H | H | 4-F | — |
| 12 | 4-Cl—Ph | 3 | H | H | H | 4-Me | — |
| 13 | 4-Cl—Ph | 3 | H | H | H | 2-Me | — |
| 14 | 4-Me—Ph | 4 | H | H | H | 3-F | — |
| 15 | 4-Me—Ph | 2 | H | H | H | 3-F | — |
| 16 | 3-MeO—Ph | 2 | H | H | H | 3-F | — |
| 17 | 3-MeO—Ph | 4 | H | H | H | 3-F | HCl (1:1) |
| 18 | Ph | 4 | H | H | H | 3-F | HCl (1:1) |
| 19 | 3-MeO—Ph | 3 | H | H | H | 2-F | — |
| 20 | Ph | 2 | H | H | H | 3-F | HCl (1:1) |
| 21 | 4-Me—Ph | 3 | H | H | H | 2-F | — |
| 22 | 4-Cl—Ph | 3 | H | Me | H | 6-F | — |
| 23 | 4-Cl—Ph | 3 | H | H | H | 6-F | — |
| 24 | 4-Cl—Ph | 3 | H | H | H | 6-MeO | — |
| 25 | 4-Cl—Ph | 3 | H | Me | H | 6-MeO | — |
| 26 | 4-Cl—Ph | 3 | H | H | H | 5-$CH_2OH$ | — |
| 27 | 2-Naphthyl | 3 | H | H | H | 2-F | — |
| 28 | Ph | 3 | H | H | H | 2-F | HCl (1:1) |
| 29 | 4-Cl—Ph | 3 | H | Me | H | 6-F | +18.1 (c = 0.502, methanol); +13.3 (c = 0.446, DMSO). |
| 30 | 4-Cl—Ph | 3 | H | Me | H | 6-F | −13.2 (c = 0.318, methanol); −13.5 (c = 0.308, DMSO). |
| 31 | 2,4-diF—Ph | 2 | H | H | H | 3-F | — |
| 32 | 2,4-diF—Ph | 3 | H | H | H | 2,4-diF | — |
| 33 | 3-MeO—Ph | 3 | H | Me | Me | 6-F | — |
| 34 | 3-MeO—Ph | 3 | H | Me | H | 6-F | — |
| 35 | 4-Cl—Ph | 3 | H | Me | Me | 2,4-diF | — |
| 36 | 2-Naphthyl | 2 | H | Me | H | 5-F | — |

TABLE 2-continued

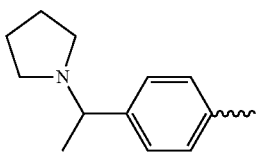

| Ex. | R₁ | R | R₄ | R₃ | R₂ | X | Salt/base |
|---|---|---|---|---|---|---|---|
| 37 | 4-Me—Ph | 3 | Me | H | H | 2,4-diF | — |
| 38 | 4-NO₂—Ph | 2 | H | H | H | 3-F | — |
| 39 | 4-(Pyrrolidin-1-yl)Ph | 3 | H | H | H | 2,4-diF | — |
| 40 | 3,4-diF—Ph | 3 | H | H | H | 2,4-diF | — |
| 41 | 2-F—Ph | 3 | H | H | H | 2,4-diF | — |
| 42 | 3-Br—Ph | 3 | H | H | H | 2,4-diF | — |
| 43 | 4-MeSO₂—Ph | 3 | H | H | H | 2,4-diF | — |
| 44 | Ph | 3 | H | Me | Me | 2-Me | — |
| 45 | 2,4-diF | 2 | H | H | —(CH₂)₂—** | | — |
| 46 | 4-Cl—Ph | 3 | MeO—(CH₂)₂ | H | H | 2,4-diF | — |
| 47 | 2,4-diF | 2 | H | Me | —(CH₂)₂—** | | — |
| 48 | 4-Cl—Ph | 3 | H | Me | Me | 2-OMe | — |
| 49 | 4-Cl—Ph | 3 | H | Me | H | 2-OMe | — |
| 50 | 4-CF₃—Ph | 2 | H | H | H | 3-F | — |
| 51 | 4-MeO—Ph | 2 | H | H | H | 3-F | — |
| 52 | 4-(Pyrrolin-1-yl)-Ph | 2 | H | H | H | 3-F | — |
| 53 | 4-F—Ph | 2 | H | H | H | 3-F | — |
| 54 | 3,4-diF—Ph | 2 | H | H | H | 3-F | — |
| 55 | 3-CN—Ph | 2 | H | H | H | 3-F | — |
| 56 | 2-F—Ph | 2 | H | H | H | 3-F | — |
| 57 | 3-Br—Ph | 2 | H | H | H | 3-F | — |
| 58 | 3-Me-4-Cl—Ph | 2 | H | H | H | 3-F | — |
| 59 | 3-Cl-4-Me—Ph | 2 | H | H | H | 3-F | — |
| 60 | 4-MeSO₂—Ph | 2 | H | H | H | 3-F | — |
| 61 | 4-MeO—Ph | 3 | H | H | H | 2,4-diF | — |
| 62 | 4-F—Ph | 3 | H | H | H | 2,4-diF | — |
| 63 | 3-CN—Ph | 3 | H | H | H | 2,4-diF | — |
| 64 | 3-Me-4-Cl—Ph | 3 | H | H | H | 2,4-diF | — |
| 64a | 3-Cl-4-Me—Ph | 3 | H | H | H | 2,4-diF | — |
| 65 | 4-MeS—Ph | 3 | H | H | H | 2,4-diF | — |
| 66 | 4-Cl—Ph | 3 | H | Me | Me | 2-Cl | — |
| 67 | 4-Cl—Ph | 3 | H | Me | H | 2-Cl | — |
| 68 | 4-Cl—Ph | 2 | H | H | H | 3-F | — |
| 69 | 4-Cl—Ph | 2 | MeO—(CH₂)₂— | H | H | 3-F | — |
| 70 | 3-MeCONH—Ph | 2 | H | H | H | 3-F | — |
| 71 | 4-(HOCH₂)—Ph | 2 | H | H | H | 3-F | — |
| 72 | 3-(HOCH₂)—Ph | 2 | H | H | H | 3-F | — |
| 73 | 4-MeSO₂NH—Ph | 2 | H | H | H | 3-F | — |
| 74 | 4-Me₂NCO—Ph | 2 | H | H | H | 3-F | — |
| 75 | 4-MeOCONH—Ph | 2 | H | H | H | 3-F | — |
| 76 | 4-MeNHCO—Ph | 2 | H | H | H | 3-F | — |
| 77 | 4-MeCONH—Ph | 2 | H | H | H | 3-F | — |
| 78 | 4-(Morpholin-4-yl)Ph | 2 | H | H | H | 3-F | — |
| 79 | 3-(Me₂NSO₂)Ph | 2 | H | H | H | 3-F | — |
| 80 | [pyrrolidinyl-ethyl-phenyl structure] | 2 | H | H | H | 3-F | — |
| 81 | 3-F-4-(Me₂NCO)—Ph | 2 | H | H | H | 3-F | — |
| 82 | 3-MeCONH—Ph | 3 | H | H | H | 2,4-diF | — |
| 83 | 4-(HOCH₂)Ph | 3 | H | H | H | 2,4-diF | — |
| 84 | 3-(HOCH₂)Ph | 3 | H | H | H | 2,4-diF | — |
| 85 | 4-Me₂NCO—Ph | 3 | H | H | H | 2,4-diF | — |
| 86 | 4-MeOCONH—Ph | 3 | H | H | H | 2,4-diF | — |
| 87 | 4-MeNHCO—Ph | 3 | H | H | H | 2,4-diF | — |
| 88 | 4-MeCONH—Ph | 3 | H | H | H | 2,4-diF | — |
| 89 | 4-(morpholin-4-yl)-Ph | 3 | H | H | H | 2,4-diF | — |
| 90 | 3-(IsPrCONH)Ph | 3 | H | H | H | 2,4-diF | — |
| 91 | 3-Me₂NSO₂—Ph | 3 | H | H | H | 2,4-diF | — |

TABLE 2-continued

| Ex. | R₁ | R | R₄ | R₃ | R₂ | X | Salt/base |
|---|---|---|---|---|---|---|---|
| 92 | 1-(4-(pyrrolidin-1-ylmethyl)phenyl) [pyrrolidinyl-CH(CH₃)-C₆H₄-] | 3 | H | H | H | 2,4-diF | — |
| 93 | 3-F-4-(Me₂NCO)—Ph | 3 | H | H | H | 2,4-diF | — |

*For compounds 8 and 9, X is in the 4 and 2 position respectively
**For compounds 45 and 47, X is in the 3 position
Compounds 29 and 30 are the enantiomers of the racemic product 22.

TABLE 3

| Ex. | M.p./[M + H] | ¹H NMR spectrum (d₆-DMSO, δ in ppm) |
|---|---|---|
| 1 | 200-202 | 4.65 (d, 2H); 5.35 (t, 1H); 7.35 (t, 1H); from 7.4 to 7.6 (m, 5H); 7.7 (d, 1H); 8.0 (d, 2H); 8.5 (s, 1H); 8.8 (s, 1H). |
| 2 | 193-195 | 1.4 (d, 3H); 5.1 (m, 1H); 5.35 (d, 1H); 7.35 (m, 1H); from 7.45 to 7.65 (m, 5H); 7.7 (d, 1H); 8.05 (d, 2H); 8.5 (s, 1H); 8.75 (s, 1H). |
| 3 | 214-216 | 4.6 (d, 2H); 5.3 (m, 1H); 7.25 (m, 1H); 7.45 (d, 1H); 7.55 (d, 2H); from 7.6 to 7.7 (m, 2H); 8.0 (d, 2H); 8.5 (s, 1H); 8.75 (s, 1H). |
| 4 | 195-197 | 1.5 (d, 3H); 5.2 (m, 1H); 5.4 (d, 1H); 7.2 (m, 1H); 7.4 (d, 1H); from 7.5 to 7.6 (m, 3H); 7.7 (d, 1H); 8.05 (d, 2H); 8.5 (s, 1H); 8.75 (s, 1H). |
| 5 | 208-210 | 1.45 (d, 3H); 5.05 (m, 1H); 5.4 (d, 1H); 7.25 (m, 1H); 7.5 (d, 2H); from 7.55 to 7.75 (m, 3H); 7.85 (m, 1H); 8.05 (d, 2H); 8.45 (s, 1H); 8.9 (s, 1H). |
| 6 | 156-156.5 | 2.4 (s, 3H); 4.55 (d, 2H); 5.2 (m, 1H); 7.2 (s, 1H); from 7.4 to 7.55 (m, 4H); 7.6 (d, 1H); 7.7 (d, 1H); 8.05 (d, 2H); 8.45 (s, 1H); 8.9 (s, 1H). |
| 7 | 156.2-157.4 | 3.85 (s, 3H); 4.55 (m, 2H); 5.3 (t, 1H); 6.95 (s, 1H); 7.15 (s, 1H); 7.25 (s, 1H); 7.55 (d, 2H); from 7.6 to 7.7 (m, 2H); 8.05 (d, 2H); 8.45 (s, 1H); 8.9 (s, 1H). |
| 8 | 232.3-233.7 | 1.75 (m, 2H); 1.95 (m, 2H); 2.75 (m, 2H); 4.65 (m, 1H); 5.2 (m, 1H); 7.2 (m, 1H); 7.5 (m, 3H); 7.6 (m, 1H); 7.7 (m, 1H); 7.75 (m, 1H); 8.05 (d, 2H); 8.45 (s, 1H); 8.85 (s, 1H). |
| 9 | 218.1-219.6 | from 1.6 to 2.0 (m, 4H); from 2.55 to 2.7 (m, 2H); 4.65 (m, 1H); 5.2 (d, 1H); 7.2 (d, 1H); from 7.25 to 7.35 (m, 2H); 7.5 (m, 3H); 7.6 (d, 1H); 8.05 (d, 2H); 8.4 (s, 1H); 8.5 (s, 1H). |
| 10 | 91.8-92.5 | 2.3 (s, 3H); 4.55 (d, 2H); 5.2 (t, 1H); from 7.25 to 7.35 (m, 4H); 7.5 (d, 2H); 7.65 (d, 1H); 8.0 (d, 2H); 8.45 (s, 1H); 8.55 (s, 1H). |
| 11 | 171.9-172.6 | 4.65 (d, 2H); 5.4 (t, 1H); 7.35 (m, 1H); 7.55 (d, 2H); 7.65 (d, 1H); from 7.7 to 7.8 (m, 2H); 7.85 (d, 1H); 8.05 (d, 2H); 8.5 (s, 1H); 8.9 (s, 1H). |
| 12 | 183.4-184.1 | 2.3 (s, 3H); 4.6 (d, 2H); 5.15 (t, 1H); 7.25 (d, 1H); 7.55 (m, 3H); 7.6 (d, 1H); from 7.65 to 7.75 (m, 2H); 8.05 (d, 2H); 8.45 (s, 1H); 8.85 (s, 1H). |
| 13 | 203.4-204 | 2.2 (s, 3H); 4.55 (d, 2H); 5.2 (t, 1H); from 7.2 to 7.35 (m, 3H); from 7.45 to 7.55 (m, 3H); 7.65 (d, 1H); 8.05 (d, 2H); 8.4 (s, 1H); 8.45 (s, 1H). |
| 14 | 222.5-223 | 2.35 (s, 3H); 4.6 (m, 2H); 5.3 (t, 1H); 7.3 (d, 2H); from 7.55 to 7.7 (m, 5H); 7.9 (d, 2H); 8.35 (s, 1H); 8.95 (s, 1H). |
| 15 | 220-221 | 2.4 (s, 3H); 4.45 (m, 2H); 5.3 (m, 1H); from 7.25 to 7.35 (m, 4H); from 7.4 to 7.55 (m, 2H); 7.65 (d, 1H); 7.9 (d, 2H); 8.4 (s, 1H); 8.65 (m, 1H). |
| 16 | 190-191 | 3.85 (s, 3H); 4.45 (m, 2H); 5.3 (m, 1H); 6.9 (m, 1H); from 7.25 to 7.5 (m, 5H); from 7.55 to 7.65 (m, 2H); 7.7 (d, 1H); 8.5 (s, 1H); 8.7 (s, 1H). |
| 17 | 281-283 | 3.9 (s, 3H); 4.65 (s, 2H); 7.1 (d, 1H); 7.55 (t, 1H); from 7.6 to 7.75 (m, 5H); 8.0 (d, 1H); 8.25 (d, 1H); 8.75 (s, 1H); 9.25 (s, 1H). |
| 18 | 305-306 | 4.65 (d, 2H); from 7.5 to 7.75 (m, 6H); 8.0 (d, 1H); 8.05 (d, 2H); 8.2 (d, 1H); 8.7 (s, 1H); 9.3 (s, 1H). |

TABLE 3-continued

| Ex. | M.p./[M + H] | ¹H NMR spectrum (d₆-DMSO, δ in ppm) |
|---|---|---|
| 19 | 143-144 | 3.85 (s, 3H); 4.65 (d, 2H); 5.35 (t, 1H); 6.95 (d, 1H); from 7.3 to 7.4 (m, 2H); 7.45 (d, 1H); from 7.5 to 7.65 (m, 4H); 7.7 (d, 1H); 8.5 (s, 1H); 8.75 (s, 1H). |
| 20 | 257-258 | 4.45 (d, 2H); from 7.3 to 7.45 (m, 2H); from 7.5 to 7.7 (m, 4H); from 8.0 to 8.15 (m, 4H); 8.9 (s, 1H); 9.0 (s, 1H). |
| 21 | 208.5-209.5 | 2.35 (s, 3H); 4.65 (d, 2H); 5.35 (t, 1H); 7.3 (d, 2H); 7.35 (m, 1H); 7.45 (d, 1H); 7.55 (m, 2H); 7.7 (d, 1H); 7.9 (d, 2H); 8.45 (s, 1H); 8.85 (s, 1H). |
| 22 | 180-182 | 1.55 (d, 3H); 5.0 (q, 1H); from 7.15 to 7.25 (m, 1H); from 7.3 to 7.6 (m, 6H); 7.75 (d, 1H); from 7.85 to 8.0 (m, 3H); 8.4 (s, 1H). |
| 23 | 228-229 | 4.55 (d, 2H); 5.25 (t, 1H); from 7.2 to 7.6 (m, 6H); 7.65 (d, 1H); 8.0 (d, 2H); 8.45 (s, 1H); 8.75 (s, 1H). |
| 24 | 200-202 | 3.85 (s, 3H); 4.7 (s, 2H); 7.05 (m, 1H); from 7.35 to 7.5 (m, 5H); 7.75 (m, 1H); from 7.85 to 8.0 (m, 3H); 8.35 (s, 1H). |
| 25 | 210-212 | 1.3 (d, 3H); 3.75 (s, 3H); 4.7 (m, 1H); 5.05 (d, 1H); 7.05 (d, 1H); from 7.3 to 7.6 (m, 6H); 7.95 (d, 2H); 8.45 (s, 1H); 8.6 (s, 1H). |
| 26 | 216-217 | 4.6 (d, 4H); 5.2 (t, 2H); 7.3 (s, 1H); 7.5 (m, 4H); from 7.6 to 7.7 (m, 2H); 7.95 (d, 2H); 8.45 (s, 1H); 8.85 (s, 1H). |
| 27 | 195-197 | 4.65 (d, 2H); 5.35 (t, 1H); 7.35 (t, 1H); from 7.45 to 7.55 (m, 5H); 7.7 (d, 1H); 7.95 (d, 1H); 8.05 (m, 2H); 8.15 (d, 1H); 8.7 (m, 2H); 8.85 (s, 1H). |
| 28 | 278-280 | 4.65 (s, 2H); 7.4 (t, 1H); from 7.55 to 7.7 (m, 5H); 8.05 (m, 4H); 8.8 (s, 1H); 9.1 (s, 1H). |
| 29 | 187-187.5 | 1.4 (s, 3H); 4.8 (m, 1H); 5.25 (s, 1H); 7.3 (t, 1H); from 7.4 to 7.55 (m, 4H); 7.6 (d, 1H); 7.7 (d, 1H); 8.0 (d, 2H); 8.5 (s, 1H); 8.8 (s, 1H) [α]_D: +18.1 (c = 0.502, methanol); +13.3 (c = 0.446, DMSO). |
| 30 | 184-185 | 1.4 (s, 3H); 4.8 (m, 1H); 5.25 (s, 1H); 7.3 (t, 1H); from 7.4 to 7.55 (m, 4H); 7.6 (d, 1H); 7.7 (d, 1H); 8.0 (d, 2H); 8.5 (s, 1H); 8.8 (s, 1H). [α]_D: -13.2 (c = 0.318, methanol); -13.5 (c = 0.308, DMSO). |
| 31 | 216.5-217.5 | 4.45 (d, 2H); 5.25 (t, 1H); from 7.2 to 7.35 (m, 3H); from 7.4 to 7.55 (m, 3H); 7.7 (d, 1H); 8.35 (m, 2H); 8.75 (s, 1H). |
| 32 | 199-199.5 | 4.6 (d, 2H); 5.35 (t, 1H); 7.25 (m, 2H); 7.4 (t, 1H); 7.45 (d, 1H); 7.65 (q, 1H); 7.75 (d, 1H); 8.35 (q, 1H); 8.4 (d, 1H); 8.85 (s, 1H). |
| 33 | 144-145 | 1.5 (s, 6H); 3.85 (s, 3H); 5.15 (s, 1H); 6.95 (d, 1H); 7.3 (t, 1H); 7.4 (t, 1H); 7.5 (d, 1H); from 7.55 to 7.65 (m, 3H); 7.7 (d, 2H); 8.5 (s, 1H); 8.8 (s, 1H). |
| 34 | 148-149 | 1.4 (d, 3H); 3.85 (s, 3H); 4.85 (m, 1H); 5.3 (s, 1H); 6.95 (d, 1H); from 7.3 to 7.5 (m, 4H); 7.6 (m, 3H); 7.7 (d, 1H); 8.5 (s, 1H); 8.8 (s, 1H). |
| 35 | 191-192 | 1.65 (s, 6H); 5.3 (s, 1H); 7.15 (m, 1H); 7.4 (m, 1H); 7.55 (m, 3H); 7.7 (m, 1H); 8.05 (d, 2H); 8.5 (s, 1H); 8.75 (s, 1H). |
| 36 | 196-197 | 1.3 (d, 3H); 4.95 (m, 1H); 5.20 (d, 1H); 7.15 (d, 1H); 7.3 (m, 2H); from 7.5 to 7.6 (m, 2H); from 7.65 to 7.75 (m, 2H); 7.95 (d, 1H); from 8.0 to 8.1 (m, 2H); 8.15 (d, 1H); from 8.55 to 8.65 (m, 3H). |
| 37 | 108-110 | 2.35 (s, 3H); 3.3 (m, 3H); 4.55 (s, 2H); from 7.25 to 7.35 (m, 3H); 7.45 (d, 1H); from 7.65 to 7.75 (m, 2H); 7.9 (d, 2H); 8.4 (s, 1H); 8.75 (s, 1H). |
| 38 | [364] | 4.45 (d, 2H); 5.3 (t, 1H); from 7.25 to 7.35 (m, 2H); from 7.45 to 7.5 (m, 2H); 7.7 (d, 1H); from 8.25 to 8.35 (m, 4H); 8.7 (s, 2H). |
| 39 | [406] | from 1.95 to 2.0 (m, 4H); from 3.3 to 3.35 (m, 4H); 4.6 (d, 2H); 5.3 (s, 1H); 6.6 (d, 2H); 7.25 (t, 1H); 7.35 (d, 1H); from 7.6 to 7.65 (m, 2H); 7.8 (d, 2H); 8.2 (s, 1H); 8.7 (s, 1H). |
| 40 | [373] | 4.6 (d, 2H); 5.35 (t, 1H); 7.25 (t, 1H); 7.45 (d, 1H); from 7.5 to 7.6 (m, 1H); from 7.6 to 7.7 (m, 2H); from 7.8 to 7.85 (m, 1H); from 7.95 to 8.05 (m, 1H); 8.5 (s, 1H); 8.75 (s, 1H). |
| 41 | [355] | 4.6 (s, 2H); 5.35 (t, 1H); 7.25 (t, 1H); from 7.3 to 75 (m, 4H); 7.6 (m, 1H); 7.7 (d, 1H); 8.3 (t, 1H); 8.4 (s, 1H); 8.8 (s, 1H). |
| 42 | [415] | 4.6 (d, 2H); 5.35 (t, 1H); 7.25 (t, 1H); from 7.4 to 7.45 (m, 2H); 7.5 (d, 1H); from 7.6 to 7.7 (m, 2H); 8.0 (d, 1H); 8.2 (s, 1H); 8.55 (s, 1H); 8.85 (s, 1H). |
| 43 | [415] | 3.25 (s, 3H); 4.6 (s, 2H); 5.35 (s, 1H); 7.25 (t, 1H); 7.45 (d, 1H); from 7.6 to 7.65 (m, 1H); 7.7 (d, 1H); 8.0 (d, 2H); 8.25 (d, 2H); 8.65 (s, 1H); 8.8 (s, 1H). |
| 44 | 215-217 | 1.6 (s, 6H); 2.5 (m, 3H); 5.0 (s, 1H); from 7.15 to 7.25 (m, 3H); 7.35 (m, 1H); 7.45 (m, 2H); 7.55 (d, 1H); 7.65 (d, 1H); 8.0 (d, 2H); 8.4 (s, 1H); 8.45 (s, 1H). |
| 45 | 210-212 | 2.0 (m, 1H); 2.2 (m, 1H); 2.8 (m, 1H); 3.25 (m, 1H); 5.15 (s, 2H); 7.25 (m, 1H); from 7.3 to 7.5 (m, 4H); 7.7 (s, 2H); 8.35 (m, 2H); 8.9 (s, 1H). |
| 46 | 135-136 | 3.25 (s, 3H); 3.5 (t, 2H); 3.65 (t, 2H); 4.6 (s, 2H); from 7.25 to 7.35 (m, 1H); 7.45 (d, 1H); 7.55 (d, 2H); from 7.65 to 7.75 (m, 2H); 8.0 (d, 2H); 8.5 (s, 1H); 8.8 (s, 1H). |
| 47 | 172-174 | 1.2 (s, 3H); from 2.0 to 2.15 (m, 2H); 2.8 (m, 1H); 3.05 (m, 1H); 5.15 (s, 1H); 7.1 (m, 1H); from 7.2 to 7.35 (m, 3H); 7.4 (t, 1H); 7.55 (d, 1H); 7.65 (s, 1H); 8.35 (m, 2H); 8.65 (s, 1H). |
| 48 | 174-176 | 1.6 (s, 6H); 3.35 (s, 3H); 5.05 (s, 1H); 7.2 (t, 1H); 7.35 (d, 1H); 7.45 (d, 1H); 7.55 (d, 2H); 7.7 (m, 2H); 8.0 (d, 2H); 8.5 (s, 1H); 8.7 (s, 1H). |

TABLE 3-continued

| Ex. | M.p./[M + H] | $^1$H NMR spectrum (d$_6$-DMSO, δ in ppm) |
|---|---|---|
| 49 | 220-222 | 1.4 (d, 3H); 3.45 (s, 3H); 5.15 (m, 2H); 7.25 (t, 1H); 7.35 (d, 1H); from 7.45 to 7.6 (m, 4H); 7.65 (d, 1H); 8.05 (d, 2H); 8.5 (s, 1H); 8.75 (s, 1H). |
| 50 | [387] | 4.45 (d, 2H); 5.3 (t, 1H); 7.3 (m, 2H); 7.45 (m, 2H); 7.7 (d, 1H); 7.8 (m, 2H); 8.2 (d, 2H); 8.6 (s, 1H); 8.7 (s, 1H). |
| 51 | [349] | 3.8 (s, 3H); 4.4 (m, 2H); 5.3 (t, 1H); 7.0 (d, 2H); 7.25 (m, 2H); 7.4 (d, 1H); 7.45 (m, 1H); 7.65 (d, 1H); 7.9 (d, 2H); 8.35 (s, 1H); 8.65 (s, 1H). |
| 52 | [388] | 1.95 (m, 4H); 3.3 (m, 4H); 4.6 (d, 2H); 5.3 (t, 1H); 6.6 (d, 2H); 7.25 (m, 2H); 7.35 (d, 1H); from 7.4 to 7.5 (m, 1H); 7.6 (d, 1H); 7.8 (d, 2H); 8.2 (s, 1H); 8.6 (s, 1H). |
| 53 | [337] | 4.45 (d, 2H); 5.3 (t, 1H); 7.3 (m, 4H); from 7.4 to 7.5 (m, 2H); 7.65 (d, 1H); 8.05 (m, 2H); 8.45 (s, 1H); 8.65 (s, 1H). |
| 54 | [355] | 4.45 (d, 2H); 5.35 (t, 1H); 7.25 (m, 2H); from 7.4 to 7.55 (m, 3H); 7.65 (d, 1H); 7.85 (m, 1H); 8.0 (m, 1H); 8.5 (s, 1H); 8.7 (s, 1H). |
| 55 | [344] | 4.45 (d, 2H); 5.3 (t, 1H); 7.25 (m, 2H); 7.45 (m, 2H); 7.65 (m, 2H); 7.8 (d, 1H); 8.3 (d, 1H); 8.4 (s, 1H); 8.6 (s, 1H); 8.7 (s, 1H). |
| 56 | [337] | 4.45 (d, 2H); 5.25 (t, 1H); from 7.2 to 7.4 (m, 5H); 7.45 (m, 2H); 7.7 (d, 1H); 8.3 (t, 1H); 8.4 (s, 1H); 8.75 (s, 1H). |
| 57 | [399] | 4.45 (d, 2H); 5.3 (t, 1H); 7.25 (m, 2H); from 7.4 to 7.5 (m, 3H); 7.55 (m, 1H); 7.65 (d, 1H); 8.0 (d, 1H); 8.2 (s, 1H); 8.55 (s, 1H); 8.65 (s, 1H). |
| 58 | [367] | 2.4 (s, 3H); 4.45 (d, 2H); 5.3 (t, 1H); 7.25 (m, 2H); from 7.4 to 7.5 (m, 3H); 7.65 (d, 1H); 7.85 (m, 1H); 8.0 (d, 1H); 8.5 (m, 1H); 8.65 (m, 1H). |
| 59 | [367] | 2.35 (s, 3H); 4.45 (d, 2H); 5.35 (t, 1H); 7.25 (m, 2H); from 7.4 to 7.5 (m, 3H); 7.65 (d, 1H); 7.85 (m, 1H); 8.0 (m, 1H); 8.5 (m, 1H); 8.65 (m, 1H). |
| 60 | [397] | 3.25 (m, 3H); 4.4 (d, 2H); 5.3 (t, 1H); 7.25 (m, 2H); 7.45 (m, 2H); 7.7 (d, 1H); 8.0 (d, 2H); 8.25 (d, 2H); 8.65 (s, 1H); 8.7 (s, 1H). |
| 61 | [367] | 3.8 (s, 3H); 4.6 (d, 2H); 5.35 (t, 1H); 7.0 (d, 2H); 7.25 (t, 1H); 7.4 (d, 1H); from 7.55 to 7.65 (m, 2H); 7.9 (d, 2H); 8.35 (s, 1H); 8.75 (s, 1H). |
| 62 | [355] | 4.6 (d, 2H); 5.35 (t, 1H); from 7.2 to 7.3 (m, 3H); 7.4 (d, 1H); from 7.6 to 7.7 (m, 2H); 8.05 (m, 2H); 8.45 (s, 1H); 8.75 (s, 1H). |
| 63 | [362] | 4.6 (d, 2H); 5.35 (t, 1H); 7.25 (t, 1H); 7.45 (d, 1H); from 7.6 to 7.75 (m, 3H); 7.8 (d, 1H); 8.3 (d, 1H); 8.4 (s, 1H); 8.6 (s, 1H); 8.8 (s, 1H). |
| 64 | [385] | 2.4 (s, 3H); 4.55 (d, 2H); 5.35 (t, 1H); 7.25 (t, 1H); 7.4 (m, 1H); 7.5 (m, 1H); from 7.6 to 7.7 (m, 2H); 7.85 (m, 1H); 8.0 (m, 1H); 8.45 (m, 1H); 8.75 (m, 1H). |
| 64a | [385] | 2.35 (s, 3H); 4.55 (d, 2H); 5.35 (t, 1H); 7.25 (t, 1H); 7.4 (m, 1H); 7.5 (m, 1H); from 7.6 to 7.7 (m, 2H); 7.85 (m, 1H); 8.0 (m, 1H); 8.45 (m, 1H); 8.75 (m, 1H). |
| 65 | [383] | 2.5 (m, 3H); 4.6 (d, 2H); 5.35 (t, 1H); 7.25 (t, 1H); 7.35 (d, 2H); 7.4 (d, 1H); from 7.6 to 7.7 (m, 2H); 7.95 (d, 2H); 8.45 (s, 1H); 8.75 (s, 1H). |
| 66 | 230-231 | 1.65 (s, 6H); 5.35 (s, 1H); 7.3 (d, 1H); from 7.35 to 7.45 (m, 2H); 7.55 (d, 2H); 7.65 (d, 1H); 7.95 (d, 1H); 8.05 (d, 2H); 8.45 (s, 1H); 8.6 (s, 1H). |
| 67 | 170-172 | 1.4 (d, 3H); 5.15 (m, 1H); 5.45 (d, 1H); 7.3 (d, 1H); 7.4 (d, 1H); from 7.45 to 7.55 (m, 3H); 7.65 (d, 1H); 7.75 (d, 1H); 8.05 (d, 2H); 8.45 (s, 1H); 8.6 (s, 1H). |
| 68 | 229-230 | 4.45 (d, 2H); 5.3 (t, 1H); 7.3 (m, 2H); 7.55-7.4 (m, 4H); 7.7 (d, 1H); 8.05 (d, 2H); 8.5 (s, 1H); 8.7 (s, 1H). |
| 69 | 104-105 | 3.45 (s, 3H); 3.65 (t, 2H); 3.75 (t, 2H); 4.5 (s, 2H); 7.15 (m, 1H); 7.25 (d, 1H); 7.35 (d, 1H); 7.45 (m, 3H); 7.7 (d, 1H); 7.95 (m, 3H); 8.65 (s, 1H). |

TABLE 4

| Ex. | M.p./[M + H] | $^1$H NMR spectrum (d$_6$-DMSO, δ in ppm) |
|---|---|---|
| 70 | [376] | 2.07 (s, 3H); 4.42 (s, 2H); 5.30 (s, 1H); 7.25 (m, 2H); 7.40 (m, 1H); 7.50 (m, 3H); 7.60 (d, 1H); 7.70 (d, 1H); 8.30 (s, 1H); 8.42 (s, 1H); 8.70 (s, 1H); 10.00 (s, 1H). |
| 71 | [349] | 4.42 (s, 2H); 4.55 (s, 2H); 5.20 (s, 1H); 5.30 (s, 1H); 7.30 (m, 2H); 7.40 (d, 1H); 7.50 (m, 2H); 7.70 (d, 1H); 7.95 (d, 2H); 8.45 (s, 1H); 8.70 (s, 1H). |
| 72 | [349] | 4.42 (s, 2H); 4.58 (s, 2H); 5.30 (m, 2H); 7.30 (m, 2H); 7.45 (m, 3H); 7.60 (s, 1H); 7.7 (d, 1H); 7.85 (d, 1H); 8.0 (s, 1H); 8.52 (s, 1H); 8.75 (s, 1H). |
| 73 | [412] | 3.05 (s, 3H); 4.45 (s, 2H); 5.25 (s, 1H); 7.25 (m, 4H); 7.45 (m, 2H); 7.65 (d, 1H); 7.95 (m, 2H); 8.4 (s, 1H); 8.7 (s, 1H); 9.9 (s, 1H). |

TABLE 4-continued

| Ex. | M.p./[M + H] | $^1$H NMR spectrum (d$_6$-DMSO, δ in ppm) |
|---|---|---|
| 74 | [390] | 3.00 (s, 6H); 4.45 (s, 2H); 5.35 (s, 1H); 7.30 (m, 2H); 7.50 (m, 4H); 7.70 (d, 1H); 8.05 (d, 2H); 8.57 (s, 1H); 8.72 (s, 1H). |
| 75 | [392] | 3.70 (s, 3H); 4.45 (s, 2H); 5.30 (s, 1H); 7.30 (m, 2H); 7.50 (m, 4H); 7.65 (d, 1H); 7.90 (d, 2H); 8.38 (s, 1H); 8.68 (s, 1H); 9.80 (s, 1H). |
| 76 | [376] | 2.80 (d, 3H); 4.45 (s, 2H); 5.35 (s, 1H); 7.30 (m, 2H); 7.48 (m, 2H); 7.70 (d, 1H); 7.92 (d, 2H); 8.10 (d, 2H); 8.45 (q, 1H); 8.55 (s, 1H); 8.70 (s, 1H). |
| 77 | [376] | 2.10 (s, 3H); 4.45 (s, 2H); 5.30 (s, 1H); 7.30 (m, 2H); 7.48 (m, 2H); 7.68 (m, 3H); 7.92 (d, 2H); 8.40 (s, 1H); 8.70 (s, 1H); 10.00 (s, 1H). |
| 78 | [404] | 3.20 (m, 4H); 3.75 (m, 4H); 4.45 (s, 2H); 5.30 (s, 1H); 7.05 (m, 2H); 7.25 (m, 2H); 7.45 (m, 2H); 7.65 (d, 1H); 7.85 (m, 2H); 8.35 (s, 1H); 8.70 (s, 1H). |
| 79 | [426] | 2.70 (s, 6H); 4.40 (s, 2H); 5.30 (s, 1H); 7.30 (m, 2H); 7.45 (m, 2H); 7.70 (m, 3H); 8.30 (m, 2H); 8.70 (d, 2H). |
| 80 | [416] | 1.65 (d, 3H); from 1.8 to 1.95 (m, 4H); from 2.5 to 2.55 (m, 2H); from 2.95 to 3.05 (m, 2H); 3.2 (q, 1H); 4.45 (d, 2H); 5.35 (t, 1H); from 7.25 to 7.35 (m, 4H); from 7.4 to 7.5 (m, 2H); 7.65 (d, 1H); 8.1 (d, 2H); 8.55 (s, 1H); 8.7 (s, 1H). |
| 81 | [408] | 2.7 (m, 6H); 4.40 (s, 2H); 5.30 (m, 1H); 7.30 (m, 2H); 7.45 (m, 2H); 7.75 (m, 2H); 7.85 (m, 2H); 8.60 (s, 1H); 8.70 (s, 1H). |
| 82 | [394] | 2.1 (s, 3H); 4.60 (s, 2H); 5.3 (m, 1H); 7.25 (m, 1H); 7.40 (m, 1H); 7.60 (m, 4H); 7.75 (s, 1H); 8.3 (s, 1H); 8.45 (m, 1H); 8.85 (s, 1H); 10 (s, 1H). |
| 83 | [367] | 4.55 (s, 2H); 4.60 (s, 2H); 5.2 (m, 1H); 5.35 (m, 1H); 7.25 (t, 1H); 7.40 (m, 3H); 7.65 (m, 2H); 7.95 (m, 2H); 8.45 (s, 1H); 8.75 (s, 1H). |
| 84 | [367] | 4.55 (m, 4H); 5.30 (m, 2H); 7.25 (m, 2H); 7.45 (m, 2H); 7.60 (m, 1H); 7.70 (m, 1H); 7.85 (d, 1H); 7.95 (s, 1H); 8.45 (s, 1H); 8.75 (s, 1H). |
| 85 | [408] | 2.95 (s, 6H); 4.60 (d, 2H); 5.35 (t, 1H); 7.25 (t, 1H); 7.45 (m, 3H); 7.65 (m, 2H); 8.05 (m, 2H); 8.50 (s, 1H); 8.75 (m, 1H). |
| 86 | [410] | 3.70 (s, 3H); 4.55 (s, 2H); 5.35 (m, 1H); 7.25 (m, 1H); 7.4 (m, 1H); 7.55 (d, 2H); 7.65 (m, 2H); 7.90 (d, 2H); 8.35 (s, 1H); 8.75 (s, 1H); 9.80 (s; 1H). |
| 87 | [394] | 2.80 (d, 3H); 4.60 (d, 2H); 5.85 (t, 1H); 7.25 (t, 1H); 7.45 (m, 1H); 7.65 (m, 1H); 7.70 (d, 1H); 7.90 (d, 2H); 8.05 (d, 2H); 8.45 (m, 1H); 8.55 (s, 1H); 8.75 (s, 1H). |
| 88 | [394] | 2.05 (s, 3H); 4.60 (d, 2H); 5.35 (t, 1H); 7.25 (t, 1H); 7.40 (d, 1H); 7.65 (m, 4H); 7.90 (d, 2H); 8.35 (s, 1H); 8.75 (s, 1H); 10.0 (s, 1H). |
| 89 | [422] | 3.2 (m, 4H); 3.75 (m, 4H); 4.6 (m, 2H); 5.35 (m, 1H); 7.03 (d, 2H); 7.27 (m, 1H); 7.5 (m, 1H); 7.68 (m, 2H); 7.84 (d, 2H); 8.37 (s, 1H); 8.78 (s, 1H). |
| 90 | [422] | 1.12 (d, 6H); 2.6 (d, 1H); 4.6 (t, 2H); 5.35 (m, 1H); 7.22 (m, 1H); 7.35 (m, 1H); 7.42 (m, 1H); 7.63 (m, 4H); 8.3 (s, 1H); 8.4 (s, 1H); 8.78 (s, 1H); 9.98 (s, 1H). |
| 91 | [444] | 2.68 (s, 6H); 4.6 (m, 2H); 5.35 (m, 1H); 7.25 (m, 1H); 7.47 (d, 1H); 7.62 (m, 1H); 7.72 (m, 3H); 8.3 (d, 1H); 8.35 (s, 1H); 8.65 (s, 1H); 8.79 (s, 1H). |
| 92 | [434] | 1.65 (d 3H); from 1.8 to 2.05 (m, 4H); from 2.5 to 2.6 (m, 2H); from 2.9 to 3.0 (m, 2H); 3.2 (q, 1H); 4.6 (d, 2H); 5.35 (t, 1H); 7.25 (m, 2H); 7.4 (m, 1H); from 7.55 to 7.7 (m, 4H); 8.1 (d, 1H); 8.5 (s, 1H); 8.75 (s, 1H). |
| 93 | [426] | 2.9 (s, 6H); 4.58 (m, 2H); 5.35 (m, 1H); 7.28 (m, 1H); 7.5 (m, 2H); 7.7 (m, 3H); 7.9 (m, 1H); 8.6 (s, 1H); 8.79 (s, 1H). |

The compounds according to the invention have formed the subject of pharmacological assays which make it possible to determine their modulatory effect on NOT.

Evaluation of the In Vitro Activity on N2A Cells

The activity of the compounds according to the invention was evaluated on a cell line (N2A) endogenously expressing the mouse Nurr1 receptor and stably transfected with the NOT binding response element (NBRE) coupled to the luciferase reporter gene. The $EC_{50}$ values are between 0.01 and 10 μM. The assays were carried out according to the procedure described below.

The Neuro-2A cell line comes from a standard commercial source (ATCC). The Neuro-2A clone was obtained, from a spontaneous tumour originating from an A albino mouse strain, by R. J Klebe et al. This Neuro-2A line is subsequently stably transfected with 8NBRE-luciferase. The N2A-8NBRE cells are cultured until confluence in 75 cm$^2$ culture flasks containing DMEM supplemented with 10% of foetal calf serum, 4.5 g/l of glucose and 0.4 mg/ml of geneticin. After a week of culture, the cells are recovered with 0.25% trypsin for 30 seconds and then resuspended in DMEM without phenol red, containing 4.5 g/l of glucose and 10% of Hyclone delipidized serum, and deposited into transparent-bottom 96-well white plates. The cells are deposited at a rate of 60 000 per well in 75 μl for 24 hours before the addition of the products. The products are applied in 25 μl and incubated for a further 24 hours. On the day of the measurement, an equivalent volume (100 μl) of Steadylite is added to each well and then left for a period of 30 minutes in order to obtain complete cell lysis and maximum signal production. The plates are subsequently measured in a luminescence counter for microplates after having been sealed with an adhesive film. The products are prepared in the form of a stock solution at $10^{-2}$ M and then diluted in 100% of DMSO. Each product concentration is prediluted in culture medium before incubation with the cells, thus containing 0.625% final concentration of DMSO.

For example, compound Nos. 3, 8, 11, 17, 29, 33, 37, 38 and 42 showed an $EC_{50}$ value of 0.5, 42, 7.5, 93, 0.1, 25, 74, 211 and 1 nM respectively. It is thus apparent that the compounds according to the invention have a modulatory effect on NOT.

The compounds according to the invention can thus be used in the preparation of medicaments for their therapeutic application in the treatment or prevention of diseases involving NOT receptors.

Thus, according to another of its aspects, a subject-matter of the invention is medicaments which comprise a compound of formula (I) or an addition salt of the latter with a pharmaceutically acceptable acid.

These medicaments are employed therapeutically, in particular in the treatment and prevention of neurodegenerative diseases, such as, for example, Parkinson's disease, Alzheimer's disease or tauopathies (for example, progressive supranuclear palsy, frontotemporal dementia, corticobasal degeneration or Pick's disease); cerebral traumas, such as ischaemia and cranial traumas and epilepsy; psychiatric diseases, such as schizophrenia, depression, substance dependence or attention deficit hyperactivity disorders; inflammatory diseases of the central nervous system, such as multiple sclerosis, encephalitis, myelitis and encephalomyelitis, and other inflammatory diseases, such as vascular pathologies, atherosclerosis, inflammations of the joints, arthrosis or rheumatoid arthritis; osteoarthritis, Crohn's disease, ulcerative colitis; allergic inflammatory diseases, such as asthma; autoimmume diseases, such as type 1 diabetes, lupus, scleroderma, Guillain-Barré syndrome, Addison's disease and other immune-mediated diseases; osteoporosis; or cancers.

These compounds might also be used as treatment associated with stem cell transplants and/or grafts.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt of the said compound, and also at least one pharmaceutically acceptable excipient.

The said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, can be administered in unit administration form, as a mixture with conventional pharmaceutical excipients, to animals and human beings for the prophylaxis or treatment of the above disorders or diseases.

The appropriate unit administration forms comprise oral forms, such as tablets, soft or hard gelatin capsules, powders, granules and oral solutions or suspensions, forms for sublingual, buccal, intratracheal, intraocular or intranasal administration or for administration by inhalation, forms for topical, transdermal, subcutaneous, intramuscular or intravenous administration, forms for rectal administration and implants. For topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

There may be specific cases where higher or lower dosages are appropriate; such dosages do not depart from the scope of the invention. According to the usual practice, the dosage appropriate to each patient is determined by the physician according to the method of administration and the weight and the response of the said patient.

The present invention, according to another of its aspects, also relates to a method for the treatment of the pathologies indicated above which comprises the administration, to a patient, of an effective dose of a compound according to the invention or one of its pharmaceutically acceptable salts.

What is claimed is:
1. A compound of formula (I):

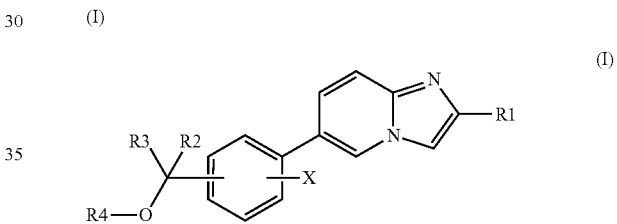

(I)

wherein:
$R_1$ represents:
  a phenyl group or a naphthyl group, wherein these two groups are optionally substituted by one or more atoms or groups chosen, independently of one another, from the following atoms or groups: halogen, $(C_1-C_{10})$alkyl, halo$(C_1-C_{10})$alkyl, $(C_1-C_{10})$alkoxy, halo$(C_1-C_{10})$alkoxy, $(C_1-C_{10})$thioalkyl, —S(O)$(C_1-C_{10})$alkyl, —S(O)$_2$$(C_1-C_{10})$alkyl, hydroxyl, cyano, nitro, hydroxy$(C_1-C_{10})$alkylene, NRaRb$(C_1-C_{10})$alkylene, $(C_1-C_{10})$alkoxy$(C_1-C_{10})$alkyleneoxy, NRaRb, CONRaRb, SO$_2$NRaRb, NRcCORd, OC(O)NRaRb, OCO$(C_1-C_{10})$alkyl, NRcC(O)ORe, NRcSO$_2$Re, aryl$(C_1-C_{10})$alkylene, monocyclic aryl or monocyclic heteroaryl, wherein the monocyclic aryl or monocyclic heteroaryl are optionally substituted by one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, oxo, nitro, cyano or OCO$(C_1-C_{10})$alkyl group;

X represents from 1 to 4 substituents which are identical to or different from one another and which are chosen from halogen, $(C_1-C_{10})$alkyl, $(C_1-C_{10})$alkoxy, NRaRb, cyano and nitro, wherein the $(C_1-C_{10})$alkyl is optionally substituted by one or more groups chosen from a halogen, $(C_1-C_{10})$alkoxy, halo$(C_1-C_{10})$alkoxy, NRaRb and hydroxyl;

$R_2$ and $R_3$ represent, independently of one another,
a hydrogen atom,
a $(C_1-C_{10})$alkyl group, this group being optionally substituted by an Rf group; or an aryl group, optionally substituted by one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;
$R_2$ and X can together form, with the carbon atoms which carry them, a carbon ring of 5 to 7 carbon atoms;
$R_4$ represents:
a hydrogen atom,
a $(C_1-C_{10})$alkyl group, this group being optionally substituted by an Rf group; or an aryl group, optionally substituted by one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano, $(C_1-C_{10})$alkyl(CO)—, CONRaRb, NRcCORd, OC(O)NRaRb, OCO$(C_1-C_{10})$alkyl, NRcC(O)ORe or aryl group, wherein the aryl is optionally substituted by one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;
Ra and Rb represent, independently of one another,
a hydrogen atom or a $(C_1-C_{10})$alkyl, aryl$(C_1-C_{10})$alkylene or aryl group;
or Ra and Rb together form, with the nitrogen atom which carries them, an azetidine, pyrrolidine, piperidine, azepine, morpholine, thiomorpholine, piperazine or homopiperazine group, this group being optionally substituted by a $(C_1-C_{10})$alkyl, aryl or aryl$(C_1-C_{10})$alkylene group;
Rc and Rd represent, independently of one another,
a hydrogen atom or a $(C_1-C_{10})$alkyl, aryl$(C_1-C_{10})$alkylene or aryl group;
or Rc and Rd together form a $(C_2-C_5)$alkylene group;
Re represents
a $(C_1-C_{10})$alkyl, aryl$(C_1-C_{10})$alkylene or aryl group;
or Rc and Re together form a $(C_2-C_5)$alkylene group; and
Rf represents
a halogen atom or a $(C_1-C_{10})$alkoxy, halo$(C_1-C_{10})$alkoxy, hydroxyl, cyano, NRaRb, C(O)NRaRb, NRcCORd, OC(O)NRaRb, OCO$(C_1-C_{10})$alkyl, NRcCOORe, SO$_2$NRaRb, NRcSO$_2$Re, aryl$(C_1-C_{10})$alkylene or aryl group, wherein the aryl is optionally substituted by one or more substituents chosen from a halogen or a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano or OCO$(C_1-C_{10})$alkyl group;
or an acid addition salt thereof.

2. The compound of formula (I) according to claim 1, wherein:
$R_1$ represents a phenyl group or a naphthyl group optionally substituted by one or more atoms or groups chosen, independently of one another, from halogen atoms and $(C_1-C_{10})$alkyl, $(C_1-C_{10})$alkoxy, nitro, —S(O)$_2(C_1-C_{10})$alkyl, halo$(C_1-C_{10})$alkyl, cyano, $(C_1-C_{10})$thioalkyl, NRaRb, NRcCORd, hydroxy$(C_1-C_{10})$alkylene, NRcSO$_2$Re, CONRaRb, NRcC(O)ORe, SO$_2$NRaRb or NRaRb$(C_1-C_{10})$alkylene groups;
Ra and Rb represent, independently of one another, a hydrogen atom or a $(C_1-C_{10})$alkyl group;
or Ra and Rb together form, with the nitrogen atom which carries them, a pyrrolidinyl or morpholinyl group;
Rc and Rd represent, independently of one another, a hydrogen atom or a $(C_1-C_{10})$alkyl group; and Re represents a $(C_1-C_{10})$alkyl group;
or an acid addition salt thereof.

3. The compound of formula (I) according to claim 1, wherein:
X represents 1 or 2 substituents, identical to or different from one another, chosen from halogen, $(C_1-C_{10})$alkyl or $(C_1-C_{10})$alkoxy, it being possible for $(C_1-C_{10})$alkyl to be optionally substituted by a hydroxyl group;
$R_2$ and X can together form, with the carbon atoms which carry them, a carbon ring of 5 or 6 carbons;
or an acid addition salt thereof.

4. The compound of formula (I) according claim 1, wherein:
$R_2$ and $R_3$ represent, independently of one another, a hydrogen atom or a $(C_1-C_{10})$alkyl group;
or an acid addition salt thereof.

5. The compound of formula (I) according to claim 1, wherein:
$R_4$ represents a hydrogen atom or a $(C_1-C_{10})$alkyl group, this group optionally being substituted by an Rf group; and
Rf represents a $(C_1-C_{10})$alkoxy group;
or an acid addition salt thereof.

6. The compound of formula (I) according to claim 1, wherein:
the substitution of the

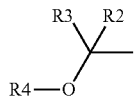

group on the phenyl ring is in the 2, 3 or 4 position; or an acid addition salt thereof.

7. The compound of formula (I) according to claim 1, wherein:
$R_1$ represents a phenyl group or a naphthyl group, optionally substituted by one or more atoms or groups chosen, independently of one another, from halogen atoms and $(C_1-C_{10})$alkyl, $(C_1-C_{10})$alkoxy, nitro, —S(O)$_2(C_1-C_{10})$alkyl, halo$(C_1-C_{10})$alkyl, cyano, $(C_1-C_{10})$thioalkyl, NRaRb, NRcCORd, hydroxy$(C_1-C_{10})$alkylene, NRcSO$_2$Re, CONRaRb, NRcC(O)ORe, SO$_2$NRaRb or NRaRb$(C_1-C_{10})$alkylene groups;
Ra and Rb represent, independently of one another, a hydrogen atom or a $(C_1-C_{10})$alkyl group;
or Ra and Rb together form, with the nitrogen atom which carries them, a pyrrolidinyl or morpholinyl group;
Rc and Rd represent, independently of one another, a hydrogen atom or a $(C_1-C_{10})$alkyl group;
Re represents a $(C_1-C_{10})$alkyl group;
X represents 1 or 2 substituents, identical to or different from one another, chosen from halogen, $(C_1-C_{10})$alkyl, and $(C_1-C_{10})$alkoxy, wherein the $(C_1-C_{10})$alkyl group is optionally substituted by a hydroxyl group;
$R_2$ and X can together form, with the carbon atoms which carry them, a carbon ring of 5 or 6 carbons;
$R_2$ and $R_3$ represent, independently of one another, a hydrogen atom or a $(C_1-C_{10})$alkyl group;
$R_4$ represents a hydrogen atom or a $(C_1-C_{10})$alkyl group, this group being optionally substituted by an Rf group;

Rf represents a $(C_1-C_{10})$alkoxy group; and
the substitution of the

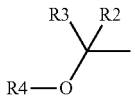

group on the phenyl ring is in the 2, 3 or 4 position;
or an acid addition salt thereof.

8. The compound of formula (I) according to claim 1, wherein:

$R_1$ represents a phenyl group optionally substituted by a halogen or a $(C_1-C_{10})$alkyl or $(C_1-C_{10})$alkoxy group;

X represents one or more halogen, $(C_1-C_{10})$alkyl, $(C_1-C_{10})$alkoxy or hydroxy$(C_1-C_{10})$alkyl;

$R_2$ and $R_3$ represent, independently of one another, a hydrogen atom or a $(C_1-C_{10})$alkyl group;

$R_2$ and X can together form, with the carbon atoms which carry them, a carbon ring of 6 carbon atoms; and $R_4$ represents a hydrogen atom,
or an acid addition salt thereof.

9. A compound selected from the group consisting of:
{3-[2-(4-Chlorophenyl)imidazo[1,2-a]pyridin-6-yl]-2-fluorophenyl}methanol;
1-{3-[2-(4-Chlorophenyl)imidazo[1,2-a]pyridin-6-yl]-2-fluorophenyl}ethanol;
{3-[2-(4-Chlorophenyl)imidazo[1,2-a]pyridin-6-yl]-2,6-difluorophenyl}methanol;
1-{3-[2-(4-Chlorophenyl)imidazo[1,2-a]pyridin-6-yl]-2,6-difluorophenyl}ethanol;
1-{5-[2-(4-Chlorophenyl)imidazo[1,2-a]pyridin-6-yl]-2-fluorophenyl}ethanol;
{3-[2-(4-Chlorophenyl)imidazo[1,2-a]pyridin-6-yl]-5-methylphenyl}methanol;
{3-[2-(4-Chlorophenyl)imidazo[1,2-a]pyridin-6-yl]-5-methoxyphenyl}methanol;
7-[2-(4-Chlorophenyl)imidazo[1,2-a]pyridin-6-yl]-1,2,3,4-tetrahydronaphth-1-ol;
5-[2-(4-Chlorophenyl)imidazo[1,2-a]pyridin-6-yl]-1,2,3,4-tetrahydronaphth-1-ol;
{3-[2-(4-Chlorophenyl)imidazo[1,2-a]pyridin-6-yl]-4-methylphenyl}methanol;
{5-[2-(4-Chlorophenyl)imidazo[1,2-a]pyridin-6-yl]-2-fluorophenyl}methanol;
{5-[2-(4-Chlorophenyl)imidazo[1,2-a]pyridin-6-yl]-2-methylphenyl}methanol;
{3-[2-(4-Chlorophenyl)imidazo[1,2-a]pyridin-6-yl]-2-methylphenyl}methanol;
[2-Fluoro-4-(2-(p-tolyl)imidazo[1,2-a]pyridin-6-yl)phenyl]methanol;
[2-Fluoro-6-(2-(p-tolyl)imidazo[1,2-a]pyridin-6-yl)phenyl]methanol;
{2-Fluoro-6-[2-(3-methoxyphenyl)imidazo[1,2-a]pyridin-6-yl]phenyl}methanol;
{2-Fluoro-4-[2-(3-methoxyphenyl)imidazo[1,2-a]pyridin-6-yl]phenyl}methanol and its hydrochloride;
[2-Fluoro-4-(2-phenylimidazo[1,2-a]pyridin-6-yl)phenyl]methanol and its hydrochloride;
{2-Fluoro-3-[2-(3-methoxyphenyl)imidazo[1,2-a]pyridin-6-yl]phenyl}methanol;
[2-Fluoro-6-(2-phenylimidazo[1,2-a]pyridin-6-yl)phenyl]methanol and its hydrochloride;
[2-Fluoro-3-(2-(p-tolyl)imidazo[1,2-a]pyridin-6-yl)phenyl]methanol;
1-{3-[2-(4-Chlorophenyl)imidazo[1,2-a]pyridin-6-yl]-4-fluorophenyl}ethanol;
{3-[2-(4-Chlorophenyl)imidazo[1,2-a]pyridin-6-yl]-4-fluorophenyl}methanol;
{3-[2-(4-Chlorophenyl)imidazo[1,2-a]pyridin-6-yl]-4-methoxyphenyl}methanol;
1-{3-[2-(4-Chlorophenyl)imidazo[1,2-a]pyridin-6-yl]-4-methoxyphenyl}ethanol;
{3-[2-(4-Chlorophenyl)imidazo[1,2-a]pyridin-6-yl]-5-(hydroxymethyl)phenyl}methanol;
[2-Fluoro-3-[2-(naphth-2-yl)imidazo[1,2-a]pyridin-6-yl]phenyl]methanol;
[2-Fluoro-3-(2-phenylimidazo[1,2-a]pyridin-6-yl)phenyl]methanol and its hydrochloride;
(+)-1-{3-[2-(4-Chlorophenyl)imidazo[1,2-a]pyridin-6-yl]-4-fluorophenyl}ethanol;
(−)-1-{3-[2-(4-Chlorophenyl)imidazo[1,2-a]pyridin-6-yl]-4-fluorophenyl}ethanol;
{2-[2-(2,4-Difluorophenyl)imidazo[1,2-a]pyridin-6-yl]-6-fluorophenyl}methanol;
{3-[2-(2,4-Difluorophenyl)imidazo[1,2-a]pyridin-6-yl]-2,6-difluorophenyl}methanol;
2-{4-Fluoro-3-[2-(3-methoxyphenyl)imidazo[1,2-a]pyridin-6-yl]phenyl}propan-2-ol;
1-{4-Fluoro-3-[2-(3-methoxyphenyl)imidazo[1,2-a]pyridin-6-yl]phenyl}ethanol;
2-{3-[2-(4-Chlorophenyl)imidazo[1,2-a]pyridin-6-yl]-2,6-difluorophenyl}propan-2-ol;
1-[4-Fluoro-2-(2-(naphth-2-yl)imidazo[1,2-a]pyridin-6-yl)phenyl]ethanol;
6-(2,4-Difluoro-3-methoxymethylphenyl)-2-(p-tolyl)imidazo[1,2-a]pyridine;
{2-Fluoro-6-[2-(4-nitrophenyl)imidazo[1,2-a]pyridin-6-yl]phenyl}methanol;
{2,6-Difluoro-3-[2-(4-(pyrrolidin-1-yl)phenyl)imidazo[1,2-a]pyridin-6-yl]phenyl}methanol;
{3-[2-(3,4-Difluorophenyl)imidazo[1,2-a]pyridin-6-yl]-2,6-difluorophenyl}methanol;
{2,6-Difluoro-3-[2-(2-fluorophenyl)imidazo[1,2-a]pyridin-6-yl]phenyl}methanol;
{3-[2-(3-Bromophenyl)imidazo[1,2-a]pyridin-6-yl]-2,6-difluorophenyl}methanol;
{2,6-Difluoro-3-[2-(4-methylsulphonylphenyl)imidazo[1,2-a]pyridin-6-yl]phenyl}methanol;
2-[2-Methyl-3-(2-phenylimidazo[1,2-a]pyridin-6-yl)phenyl]propan-2-ol;
7-[2-(2,4-Difluorophenyl)imidazo[1,2-a]pyridin-6-yl]indan-1-ol;
2-(4-Chlorophenyl)-6-[2,4-difluoro-3-[(2-methoxyethyl)oxymethyl]phenyl]imidazo[1,2-a]pyridine;
7-[2-(2,4-Difluorophenyl)imidazo[1,2-a]pyridin-6-yl]-1-methylindan-1-ol;
2-{3-[2-(4-Chlorophenyl)imidazo[1,2-a]pyridin-6-yl]-2-methoxyphenyl}propan-2-ol;
1-{3-[2-(4-Chlorophenyl)imidazo[1,2-a]pyridin-6-yl]-2-methoxyphenyl}ethanol;
{2-Fluoro-6-[2-(4-trifluoromethylphenyl)imidazo[1,2-a]pyridin-6-yl]phenyl}methanol;
{2-Fluoro-6-[2-(4-methoxyphenyl)imidazo[1,2-a]pyridin-6-yl]phenyl}methanol;
{2-Fluoro-6-[2-(4-(pyrrolidin-1-yl)phenyl)imidazo[1,2-a]pyridin-6-yl]phenyl}methanol;
{2-Fluoro-6-[2-(4-fluorophenyl)imidazo[1,2-a]pyridin-6-yl]phenyl}methanol;
{2-[2-(3,4-Difluorophenyl)imidazo[1,2-a]pyridin-6-yl]-6-fluorophenyl}methanol;

3-[6-(3-Fluoro-2-hydroxymethylphenyl)imidazo[1,2-a]pyridin-2-yl]benzonitrile;
{2-Fluoro-6-[2-(2-fluorophenyl)imidazo[1,2-a]pyridin-6-yl]phenyl}methanol;
{2-[2-(3-Bromophenyl)imidazo[1,2-a]pyridin-6-yl]-6-fluorophenyl}methanol;
{2-[2-(4-Chloro-3-methylphenyl)imidazo[1,2-a]pyridin-6-yl]-6-fluorophenyl}methanol;
{2-[2-(3-Chloro-4-methylphenyl)imidazo[1,2-a]pyridin-6-yl]-6-fluorophenyl}methanol;
{2-Fluoro-6-[2-(4-methylsulphonylphenyl)imidazo[1,2-a]pyridin-6-yl]phenyl}methanol;
{2,6-Difluoro-3-[2-(4-methoxyphenyl)imidazo[1,2-a]pyridin-6-yl]phenyl}methanol;
{2,6-Difluoro-3-[2-(4-fluorophenyl)imidazo[1,2-a]pyridin-6-yl]phenyl}methanol;
3-[6-(2,4-Difluoro-3-hydroxymethylphenyl)imidazo[1,2-a]pyridin-2-yl]benzonitrile;
{2,6-Difluoro-3-[2-(4-chloro-3-methylphenyl)imidazo[1,2-a]pyridin-6-yl]phenyl}methanol;
{2,6-Difluoro-3-[2-(3-chloro-4-methylphenyl)imidazo[1,2-a]pyridin-6-yl]phenyl}methanol;
{2,6-Difluoro-3-[2-(4-methylthiophenyl)imidazo[1,2-a]pyridin-6-yl]phenyl}methanol;
2-[2-Chloro-3-[2-(4-chlorophenyl)imidazo[1,2-a]pyridin-6-yl]phenyl]propan-2-ol;
1-[2-Chloro-3-[2-(4-chlorophenyl)imidazo[1,2-a]pyridin-6-yl]phenyl]ethanol;
{2-[2-(4-Chlorophenyl)imidazo[1,2-a]pyridin-6-yl]-6-fluorophenyl}methanol;
2-(4-Chlorophenyl)-6-[3-fluoro-2-[(2-methoxyethyl)oxymethyl]phenyl]imidazo[1,2-a]pyridine;
N-{3-[6-(3-Fluoro-2-hydroxymethylphenyl)imidazo[1,2-a]pyridin-2-yl]phenyl}acetamide;
{4-[6-(3-Fluoro-2-hydroxymethylphenyl)imidazo[1,2-a]pyridin-2-yl]phenyl}methanol
{3-[6-(3-Fluoro-2-hydroxymethylphenyl)imidazo[1,2-a]pyridin-2-yl]phenyl}methanol;
N-{4-[6-(3-Fluoro-2-hydroxymethylphenyl)imidazo[1,2-a]pyridin-2-yl]phenyl}methanesulphonamide;
4-[6-(3-Fluoro-2-hydroxymethylphenyl)imidazo[1,2-a]pyridin-2-yl]-N,N-dimethylbenzamide;
Methyl {4-[6-(3-fluoro-2-hydroxymethylphenyl)imidazo[1,2-a]pyridin-2-yl]phenyl}carbamate;
4-[6-(3-Fluoro-2-hydroxymethylphenyl)imidazo[1,2-a]pyridin-2-yl]-N-methylbenzamide;
N-{4-[6-(3-Fluoro-2-hydroxymethylphenyl)imidazo[1,2-a]pyridin-2-yl]phenyl}acetamide;
{2-Fluoro-6-[2-(4-(morpholin-4-yl)phenyl)imidazo[1,2-a]pyridin-6-yl]phenyl}methanol;
3-[6-(3-Fluoro-2-hydroxymethylphenyl)imidazo[1,2-a]pyridin-2-yl]-N,N-dimethylbenzenesulphonamide;
(2-Fluoro-6-{2-[4-(1-(pyrrolidin-1-yl)ethyl)phenyl]imidazo[1,2-a]pyridin-6-yl}phenyl)methanol;
2-Fluoro-4-[6-(3-fluoro-2-hydroxymethylphenyl)imidazo[1,2-a]pyridin-2-yl]-N,N-dimethylbenzamide;
N-{3-[6-(2,4-Difluoro-3-hydroxymethylphenyl)imidazo[1,2-a]pyridin-2-yl]phenyl}acetamide;
{4-[6-(2,4-Difluoro-3-hydroxymethylphenyl)imidazo[1,2-a]pyridin-2-yl]phenyl}methanol;
{3-[6-(2,4-Difluoro-3-hydroxymethylphenyl)imidazo[1,2-a]pyridin-2-yl]phenyl}methanol;
4-[6-(2,4-Difluoro-3-hydroxymethylphenyl)imidazo[1,2-a]pyridin-2-yl]-N,N-dimethylbenzamide;
Methyl {4-[6-(2,4-difluoro-3-hydroxymethylphenyl)imidazo[1,2-a]pyridin-2-yl]phenyl}carbamate;
4-[6-(2,4-Difluoro-3-hydroxymethylphenyl)imidazo[1,2-a]pyridin-2-yl]-N-methylbenzamide;
N-{4-[6-(2,4-Difluoro-3-hydroxymethylphenyl)imidazo[1,2-a]pyridin-2-yl]phenyl}acetamide;
{2,6-Difluoro-3-[2-(4-(morpholin-4-yl)phenyl)imidazo[1,2-a]pyridin-6-yl]-phenyl}methanol;
N-{3-[6-(2,4-Difluoro-3-hydroxymethylphenyl)imidazo[1,2-a]pyridin-2-yl]phenyl}isobutyramide;
3-[6-(2,4-Difluoro-3-hydroxymethylphenyl)imidazo[1,2-a]pyridin-2-yl]-N,N-dimethylbenzenesulphonamide;
(2,6-Difluoro-3-{2-[4-(1-(pyrrolidin-1-yl)ethyl)phenyl]imidazo[1,2-a]pyridin-6-yl}phenyl)methanol; and
4-[6-(2,4-Difluoro-3-hydroxymethylphenyl)imidazo[1,2-a]pyridin-2-yl]-2-fluoro-N,N-dimethylbenzamide;
or an acid addition salt thereof.

10. A pharmaceutical composition comprising a compound of formula (I) according to claim 1 or a pharmaceutically acceptable salt thereof, and one or more pharmaceutically acceptable excipients.

11. A pharmaceutical composition comprising a compound of formula (I) according to claim 9 or a pharmaceutically acceptable salt thereof, and one or more pharmaceutically acceptable excipients.

12. A process for the synthesis of the compound of formula (I) according to claim 1, comprising reacting a compound of formula (II)

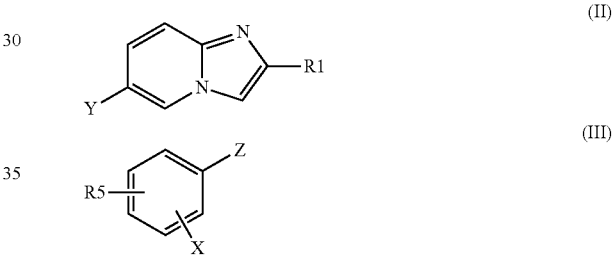

wherein R1 is as defined in claim 1 and Y represents a halogen atom or a boron derivative, with a derivative of formula (III), wherein X is defined according to claim 1 and Z represents a boron or tin derivative if Y represents a halogen atom, or else Z represents a halogen atom, if Y represents a boron derivative, and R5 represents the

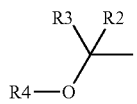

group.

13. A process for the synthesis of the compound of formula (I) according to claim 1, comprising reacting a compound of formula (VI):

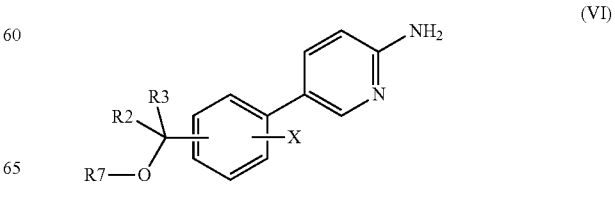

wherein R2, R3 and X are defined according to claim 1 and R7 represents R4 as defined in claim 1 or a protective group for the hydroxyl functional group PG, with a bromoketone of formula (VII):

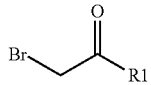
(VII)

wherein R1 is defined according to claim 1.

14. A process for the synthesis of the compound of formula (I) according to claim 1, comprising reacting a compound of formula (II):

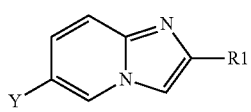
(II)

wherein R1 is defined according to claim 1 and Y represents a halogen atom or a boron derivative, with a derivative of formula (III):

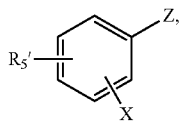
(III')

wherein X is defined according to claim 1 and Z represents a boron or tin derivative when Y represents a halogen atom, or Z represents a halogen atom when Y represents a boron derivative, and R5' represents either a carbonyl derivative $R_2CO$, in which R2 is defined according to claim 1, or an alkyl carboxylate, in order to obtain a compound of formula (IV):

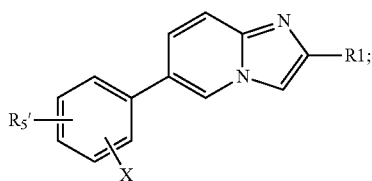
(IV)

subsequently reacting the compound of formula (IV) with an organometallic derivative in order to obtain the compound of formula (I).

15. A process for the synthesis of the compound of formula (I), comprising reacting a compound of formula (VI):

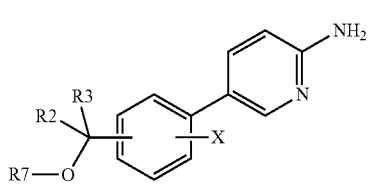
(VI)

wherein R2, R3 and X are defined according to claim 1 and R7 represents R4 as defined in claim 1 or a protective group (PG) for the hydroxyl functional group, with a bromoketone of formula (VII):

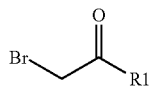
(VII)

wherein R1 is defined according to claim 1.

16. A process for the synthesis of the compound of formula (I) according to claim 1, comprising reacting a compound of formula (VI):

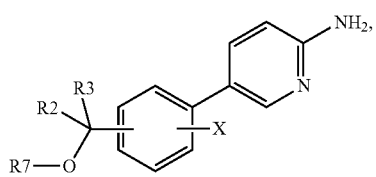
(VI)

wherein R2, R3 and X are defined according to claim 1 and R7 represents R4 as defined in claim 1 or a protective group (PG) for the hydroxyl functional group, with a bromoketone of formula (VII):

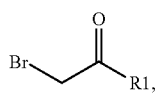
(VII)

wherein R1 is defined according to claim 1, in order to obtain a compound of formula (VIII):

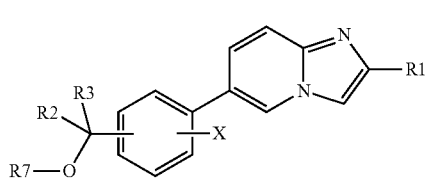
(VIII)

wherein R7 represents a protective group for the hydroxyl functional group; and
subsequently deprotecting the compound of formula (VIII) in order to obtain the compound of formula (I).

17. A process for the synthesis of the compound of formula (I) according to claim 1, comprising reacting a compound of formula (XI):

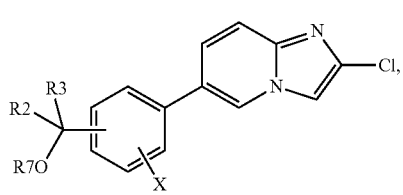
(XI)

wherein X, R2 and R3 are defined according to claim 1 and R7 represents the R4 group as defined in claim 1, with a derivative of formula (XII):

R1-Z    (XII), wherein R1 is defined according to claim 1 and Z represents a boron or tin derivative, in order to obtain the compound of formula (I).

18. A process for the synthesis of the compound of formula (I) according to claim 1, comprising reacting a compound of formula (XI):

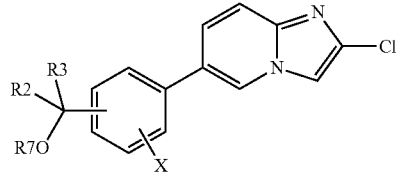

(XI)

wherein X, R2 and R3 are defined according to claim 1 and R7 represents a protective group for the hydroxyl functional group, with a derivative of formula (XII):

R1-Z    (XII), wherein R1 is defined according to claim 1 and Z represents a boron or tin derivative, in order to obtain the compounds of formula (VIII):

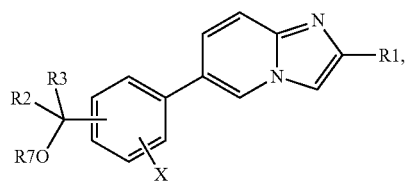

(VIII)

wherein R1, R2, R3 and X are defined according to claim 1 and R4 represents a hydrogen atom; and
subsequently deprotecting the compound of formula (VIII).

19. A compound selected from the group consisting of:

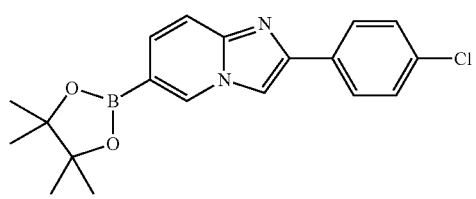

(IIa)

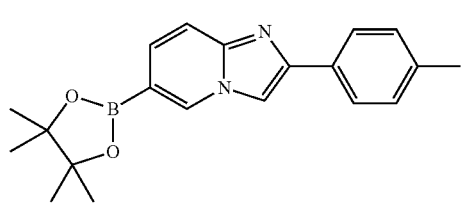

(IIb)

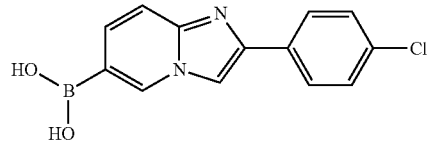

(IIc)

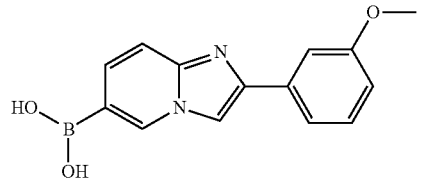

(IId)

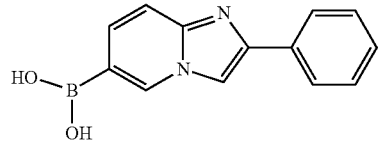

(IIe)

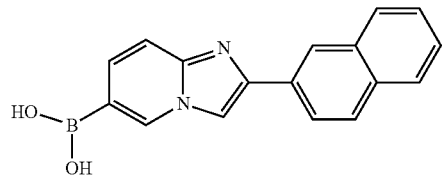

(IIf)

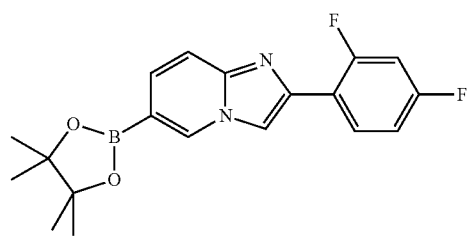

(IIg)

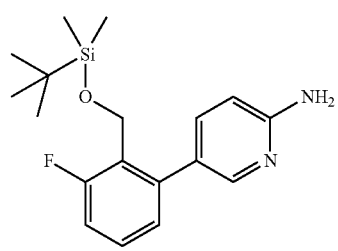

(VIa)

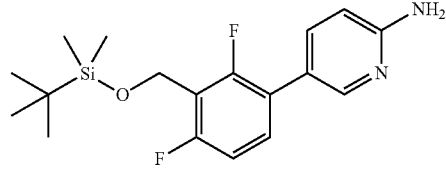

(VIb)

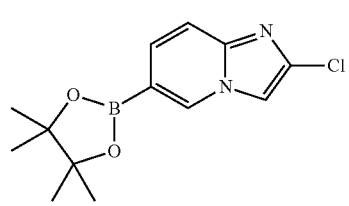

(Xa)

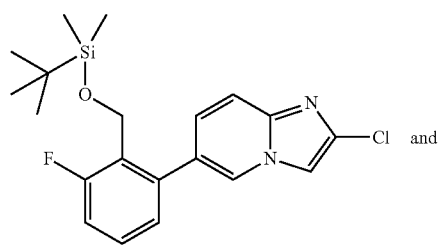
(XIa)
and
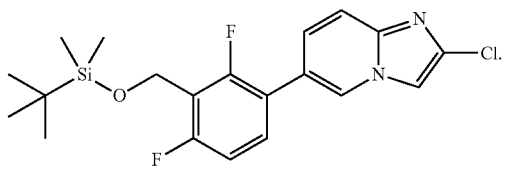
(XIb)
\* \* \* \* \*